(12) United States Patent
Zheng et al.

(10) Patent No.: US 6,825,044 B2
(45) Date of Patent: Nov. 30, 2004

(54) METHOD FOR ADJUSTING A BLOOD ANALYTE MEASUREMENT

(75) Inventors: Peng Zheng, Alameda, CA (US); Jennifer H. Gable, Walnut Creek, CA (US); W. Dale Hall, Oakland, CA (US); Kenneth G. Witte, San Jose, CA (US); James R. Braig, Piedmont, CA (US)

(73) Assignee: Optiscan Biomedical Corporation, Alameda, CA (US)

( * ) Notice: Subject to any disclaimer, the term of this patent is extended or adjusted under 35 U.S.C. 154(b) by 0 days.

(21) Appl. No.: 10/301,927

(22) Filed: Nov. 21, 2002

(65) Prior Publication Data

US 2003/0143116 A1 Jul. 31, 2003

Related U.S. Application Data

(60) Provisional application No. 60/363,941, filed on Mar. 12, 2002, and provisional application No. 60/332,125, filed on Nov. 21, 2001.

(51) Int. Cl.$^7$ .............................................. G01N 21/64
(52) U.S. Cl. .................... 436/164; 436/172; 422/82.05; 422/82.07
(58) Field of Search .......................... 436/95, 164, 171; 422/82.05–82.07; 250/252.1, 341.6, 341.8

(56) References Cited

U.S. PATENT DOCUMENTS

| | | | |
|---|---|---|---|
| 3,770,958 A | 11/1973 | Krakow | |
| 4,819,752 A | 4/1989 | Zelin | |
| 4,866,276 A | 9/1989 | Leavens et al. | |
| 4,990,772 A | 2/1991 | Rosenthal | |
| 5,059,394 A | 10/1991 | Phillips et al. | |
| 5,068,536 A | 11/1991 | Rosenthal | |
| 5,070,242 A | 12/1991 | McClelland et al. | |
| 5,070,874 A | 12/1991 | Barnes et al. | |
| 5,078,136 A | 1/1992 | Stone et al. | |

(List continued on next page.)

FOREIGN PATENT DOCUMENTS

| | | |
|---|---|---|
| EP | 0 160 768 | 11/1985 |
| WO | WO 96/01075 | 1/1996 |
| WO | WO 00/53085 | 9/2000 |
| WO | WO 01/30236 | 5/2001 |
| WO | WO 02/10725 | 2/2002 |

OTHER PUBLICATIONS

Klonoff, et al *Mid–Infrared Spectroscopy for Noninvasive Blood Glucose Monitoring*, http://ieee.org/organizations/pubs/newsletters/leos/apr98/midinfr., Apr. 1998, pp. 1–3.

Kevin Robinson, *Noninvasive Methods Hover on Horizon*, Biophotonics international, May/Jun. 1998, pp. 48–52.

(List continued on next page.)

*Primary Examiner*—Jeffrey R. Snay
(74) *Attorney, Agent, or Firm*—Knobbe Martens Olson & Bear LLP

(57) ABSTRACT

A device and method for determining analyte concentrations within a material sample are provided. A modulating temperature gradient is induced in the sample and resultant, emitted infrared radiation is measured at selected analyte absorbance peaks and reference wavelengths. The modulating temperature gradient is controlled by a surface temperature modulation. A transfer function relating the surface temperature modulation to a modulation of the measured infrared radiation is provided. Phase and magnitude differences in the transfer function are detected. These phase and magnitude differences, having a relationship to analyte concentration, are measured, correlated and processed to determine analyte concentration in the material sample. A method for adjusting an analyte measurement is provided. The method provides a hydration correction process for calibration and correction whereby analyte concentrations within the material sample may be determined. The hydration correction process is particularly suitable for determining blood analyte concentrations within human tissue.

11 Claims, 25 Drawing Sheets

U.S. PATENT DOCUMENTS

| | | |
|---|---|---|
| 5,115,133 A | 5/1992 | Knudson |
| 5,146,091 A | 9/1992 | Knudson |
| 5,204,532 A | 4/1993 | Rosenthal |
| 5,313,941 A | 5/1994 | Braig et al. |
| 5,324,979 A | 6/1994 | Rosenthal |
| 5,337,745 A | 8/1994 | Benaron |
| 5,379,764 A | 1/1995 | Barnes et al. |
| 5,515,847 A | 5/1996 | Braig et al. |
| 5,576,544 A | 11/1996 | Rosenthal |
| 5,606,164 A | 2/1997 | Price et al. |
| 5,615,672 A | 4/1997 | Braig et al. |
| 5,615,673 A | 4/1997 | Berger et al. |
| 5,657,754 A | 8/1997 | Rosencwaig |
| 5,747,806 A | 5/1998 | Khalil et al. |
| 5,782,755 A | 7/1998 | Chance et al. |
| 5,823,677 A | 10/1998 | Forester et al. |
| 5,836,317 A | 11/1998 | Kunst |
| 5,877,500 A | 3/1999 | Braig et al. |
| 5,900,632 A | 5/1999 | Sterling et al. |
| 6,025,597 A | 2/2000 | Sterling et al. |
| 6,049,081 A | 4/2000 | Sterling et al. |
| 6,070,093 A | 5/2000 | Oosta et al. |
| 6,072,180 A | 6/2000 | Kramer et al. |
| 6,097,975 A | 8/2000 | Petrovsky et al. |
| 6,157,041 A | 12/2000 | Thomas et al. |
| 6,161,028 A | 12/2000 | Braig et al. |
| 6,172,743 B1 | 1/2001 | Kley et al. |
| 6,196,046 B1 | 3/2001 | Braig et al. |
| 6,198,949 B1 | 3/2001 | Braig et al. |
| 6,246,892 B1 | 6/2001 | Chance |
| 6,264,622 B1 | 7/2001 | Augustine |
| 6,314,152 B2 * | 11/2001 | Kehayias ............... 376/159 |
| 6,635,491 B1 * | 10/2003 | Khalil et al. ............ 436/95 |

OTHER PUBLICATIONS

McNichols, et al., *Optical Glucose sending in biological fluids: an overview*, Journal of Biomedical Optics, Jan. 2000, vol. 5, No. 1, pp. 5–9.

Zheng, et al., *Noninvasive Glucose Determination by Oscillating Thermal Gradient Spectrometry*, Diabetes Technology & Therapeutics, vol. 2, No. 1, 2000, pp 17–25.

Optics Report, *Glucometry and Diabetes*, pub. by Breault Research Organization, www.OpticsReport.com, Volu8me 1, Issue 2, May 2001, pp. 1–4.

* cited by examiner

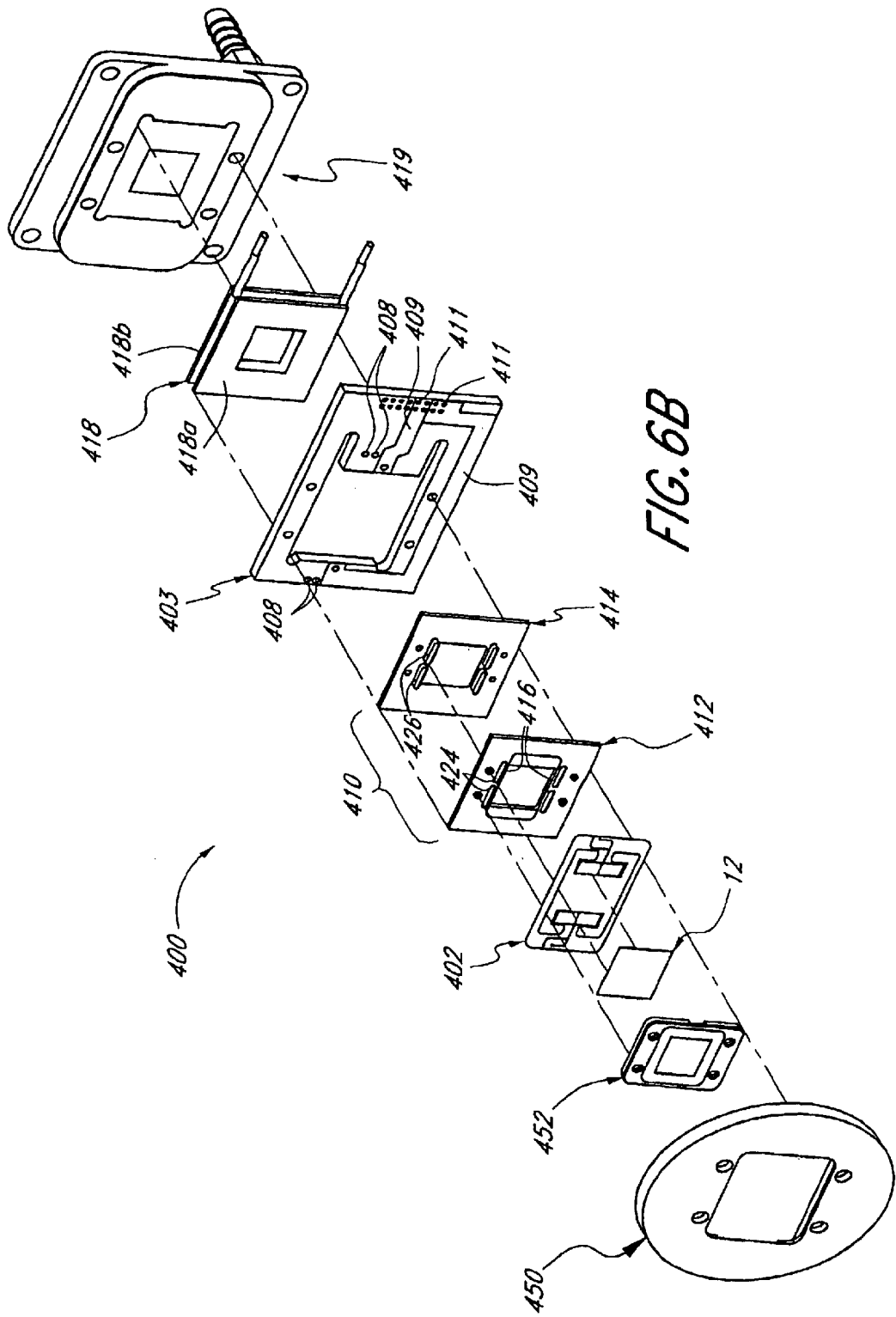

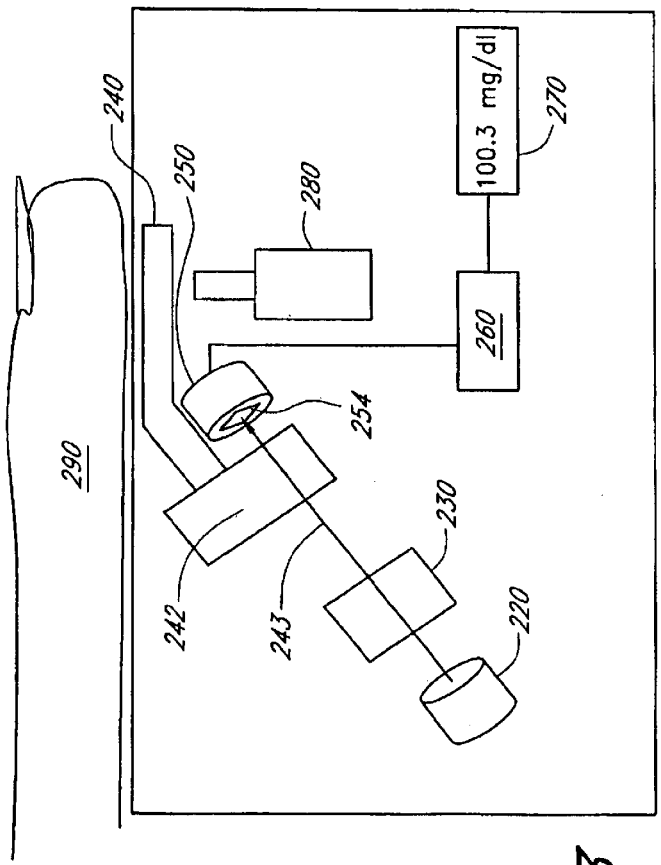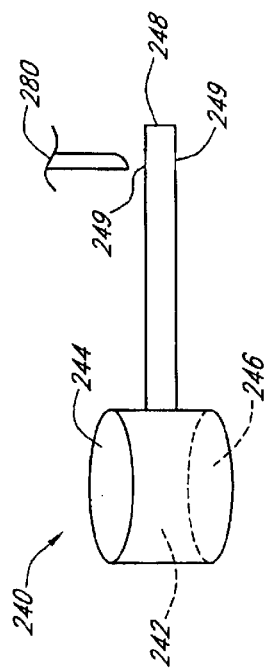
FIG. 13
FIG. 14

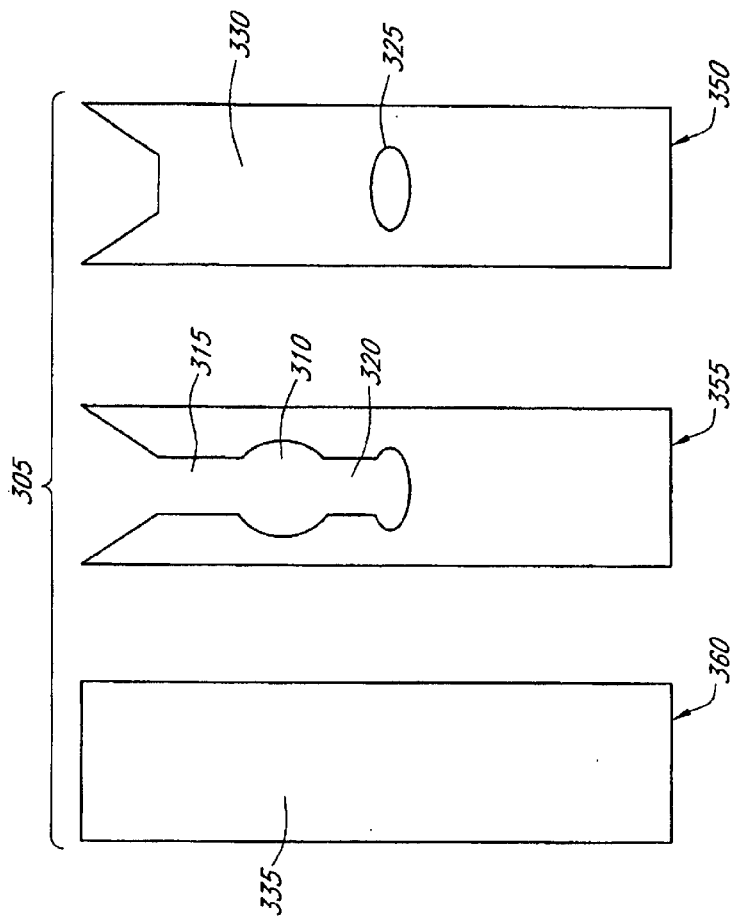
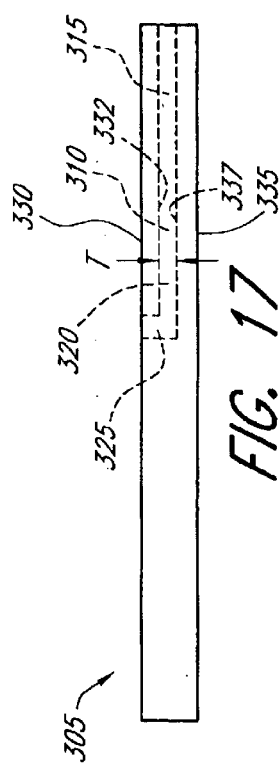
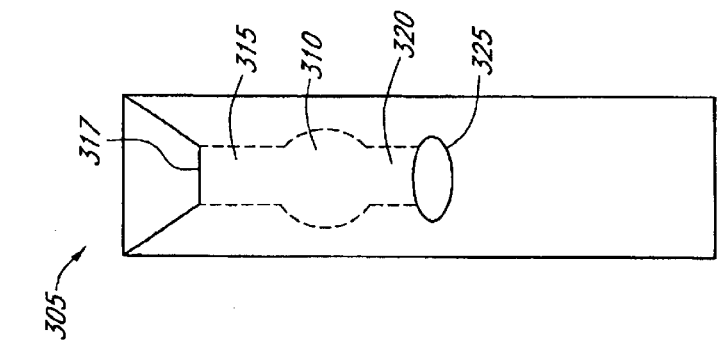

METHOD FOR ADJUSTING A BLOOD ANALYTE MEASUREMENT

RELATED APPLICATIONS

This application claims priority to U.S. Provisional Patent Application No. 60/332,125, filed Nov. 21, 2001 and No. 60/363,941, filed Mar. 12, 2002, both entitled METHOD FOR ADJUSTING A BLOOD ANALYTE MEASUREMENT, the entire contents of both of which are hereby incorporated by reference.

BACKGROUND OF THE INVENTION

1. Field of the Invention

The disclosure herein relates generally to determining analyte concentrations within a blood sample.

2. Description of the Related Art

Millions of diabetics are forced to draw blood on a daily basis to determine their blood glucose levels. In addition, the detection of other blood constituents, such as the determination of the concentration of alcohol in the bloodstream, often requires blood withdrawal in order to perform a precise analysis thereof. A search for a noninvasive methodology to accurately determine blood constituent levels has been substantially expanded in order to alleviate the discomfort of these individuals. A significant advance in the state of the art of noninvasive blood constituent analysis has been realized by the development of spectrometers, including "thermal gradient" spectrometers, which analyze the absorbance of particular wavelengths of infrared energy passed through and/or emitted by a sample of tissue. These spectroscopic analytical devices typically employ a window or lens for admitting infrared spectra into the device for analysis by infrared detectors.

Although these devices have marked a significant advance in the state of the art of noninvasive blood constituent analysis, further improvements could be made in the performance and ease of manufacture of such devices.

SUMMARY OF THE INVENTION

A device and method for determining analyte concentrations within a material sample are provided. A modulating temperature gradient is induced in the sample and resultant, emitted infrared radiation is measured at selected analyte absorbance peaks and reference wavelengths. The modulating temperature gradient is controlled by a surface temperature modulation. A transfer function relating the surface temperature modulation to a modulation of the measured infrared radiation is provided. Phase and magnitude differences in the transfer function are detected. These phase and magnitude differences, having a relationship to analyte concentration, are measured, correlated and processed to determine analyte concentration in the material sample. A method for adjusting an analyte measurement is provided. The method provides a hydration correction process for calibration and correction whereby analyte concentrations within the material sample may be determined. The hydration correction process is particularly suitable for determining blood analyte concentrations within human tissue.

In one embodiment, a method of analyzing a material sample is provided. The material sample is placed in operative engagement with an analyte detection system. The analyte detection system is operated according to an operation algorithm by which said analyte detection system determines an estimated concentration of an analyte in the material sample while reducing the effect of a hydration level of the material sample on said estimated concentration.

In another embodiment, a method of analyzing a material sample is provided. The material sample is placed in operative engagement with an analyte detection system. An estimated concentration of an analyte in the material sample is determined. The effect of a hydration level of the material sample on the estimated concentration is then reduced. Reducing the effect of the hydration level is at least partially comprised of computing a hydration correction coefficient and then computing the estimated concentration based on the hydration correction coefficient.

In one embodiment, an analyte detection system is provided. The analyte detection system comprises a detector array, a processing circuit in communication with the detector array, and a module executable by said processing circuit whereby the processing circuit computes an estimated concentration of an analyte in a material sample and reduces the effect of a hydration level of the material sample on the estimated concentration.

BRIEF DESCRIPTION OF THE DRAWINGS

FIG. 6B is an exploded perspective view of a window mounting system for use with the noninvasive optical detection system.

FIG. 13 is a schematic view of a reagentless whole-blood detection system.

FIG. 14 is a perspective view of one embodiment of a cuvette for use with the reagentless whole-blood detection system.

FIG. 15 is a plan view of another embodiment of a cuvette for use with the reagentless whole-blood detection system.

FIG. 16 is a disassembled plan view of the cuvette shown in FIG. 15.

FIG. 17 is a side view of the cuvette of FIG. 15.

DETAILED DESCRIPTION OF THE PREFERRED EMBODIMENT

Figure 1:
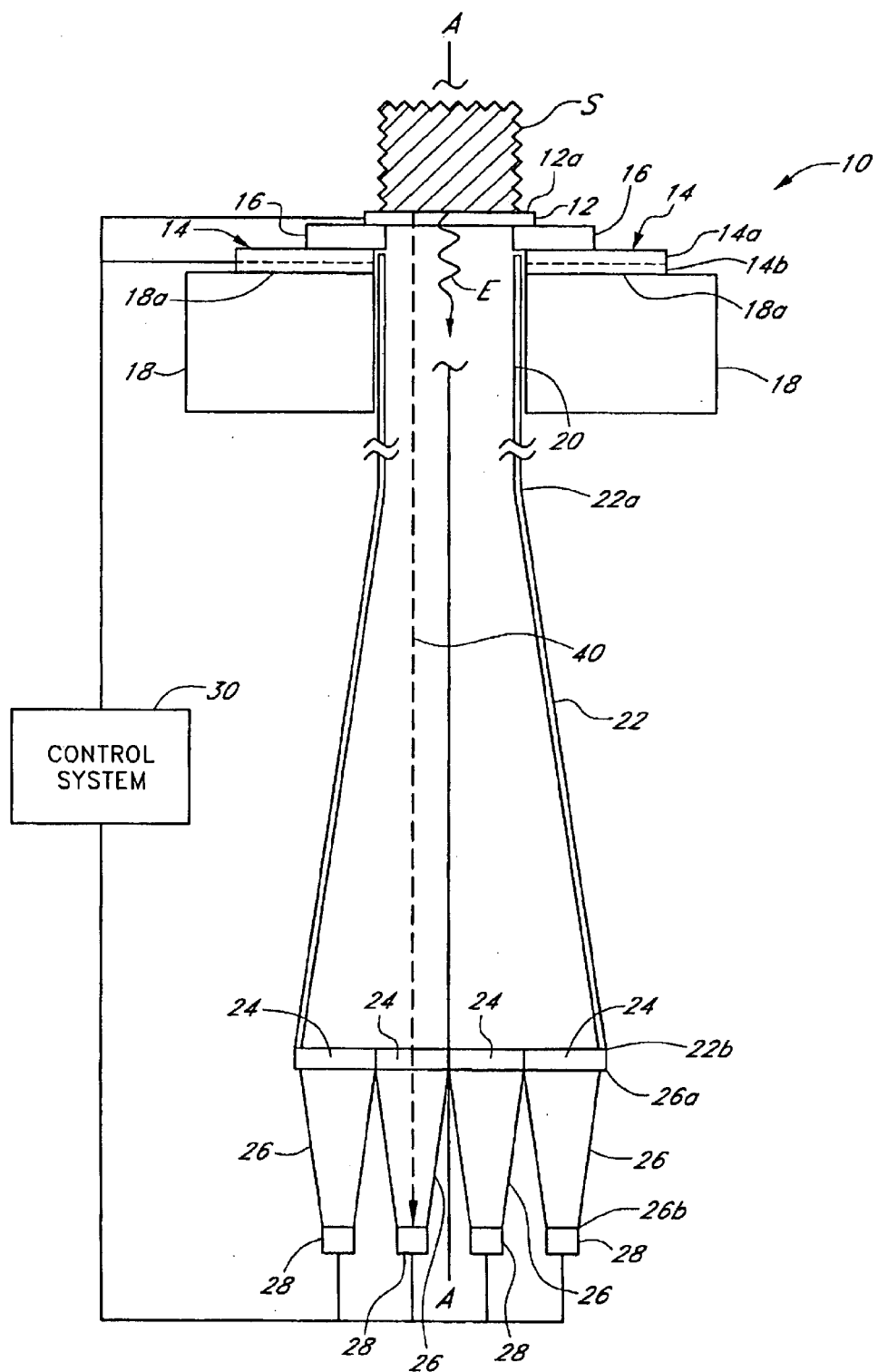
FIG. 1 is a schematic view of a noninvasive optical detection system.

Although certain preferred embodiments and examples are disclosed below, it will be understood by those skilled in the art that the invention extends beyond the specifically disclosed embodiments to other alternative embodiments and/or uses of the invention and obvious modifications and equivalents thereof. Thus, it is intended that the scope of the invention herein disclosed should not be limited by the particular disclosed embodiments described below.

When trying to measure a subject's blood glucose concentration there are many paths that can be taken. A hydration correction algorithm, described below, focuses on adjusting measurements attained by use of Mid/Far wavelength infrared (IR) radiation transmission from human tissue to measure glucose concentrations therein. Other blood constituents, or analytes, can also be measured with the hydration correction algorithm. Because skin composition varies widely from one subject to another, there are many factors that can interfere with glucose measurements. Some of these factors include skin density, fat content, pigmentation, and the hydration of the tissue itself. The hydration correction algorithm described herein provides a method of calibration and correction whereby glucose can be subtracted from a more easily identifiable measure (i.e., of water or other easily quantifiable constituent) in the tissue or fluid.

The methods and embodiments discussed herein are particularly suited for use with an apparatus taught in Assignee's U.S. Pat. No. 6,198,949, titled SOLID-STATE NONINVASIVE INFRARED ABSORPTION SPECTROMETER FOR THE GENERATION AND CAPTURE OF THERMAL GRADIENT SPECTRA FROM LIVING TISSUE, issued Mar. 6, 2001; and with the methodology taught in Assignee's U.S. Pat. No. 6,161,028, titled METHOD FOR DETERMINING ANALYTE CONCENTRATION USING PERIODIC TEMPERATURE MODULATION AND PHASE DETECTION, issued Dec. 12, 2000; as well as with the methods and apparatus taught in Assignee's U.S. patent applications Ser. No. 09/538,164, entitled METHOD AND APPARATUS FOR DETERMINING ANALYTE CONCENTRATION USING PHASE AND MAGNITUDE DETECTION OF A RADIATION TRANSFER FUNCTION; and No. 60/332,125, filed on Nov. 21, 2001, entitled METHOD FOR ADJUSTING A BLOOD ANALYTE MEASUREMENT. The entire disclosure of all of the above-mentioned patents and patent applications are hereby incorporated by reference herein and made a part of this specification.

I. Overview of Analyte Detection Systems

Disclosed herein are analyte detection systems, including a noninvasive system discussed largely in part A below and a whole-blood system discussed largely in part B below. Also disclosed are various methods, including methods for detecting the concentration of an analyte in a material sample. Both the noninvasive system/method and the whole-blood system/method can employ optical measurement. As used herein with reference to measurement apparatus and methods, "optical" is a broad term and is used in its ordinary sense and refers, without limitation, to identification of the presence or concentration of an analyte in a material sample without requiring a chemical reaction to take place. As discussed in more detail below, the two approaches each can operate independently to perform an optical analysis of a material sample. The two approaches can also be combined in an apparatus, or the two approaches can be used together to perform different steps of a method.

In one embodiment, the two approaches are combined to perform calibration of an apparatus, e.g., of an apparatus that employs a noninvasive approach. In another embodiment, an advantageous combination of the two approaches performs an invasive measurement to achieve greater accuracy and a whole-blood measurement to minimize discomfort to the patient. For example, the whole-blood technique may be more accurate than the noninvasive technique at certain times of the day, e.g., at certain times after a meal has been consumed, or after a drug has been administered.

It should be understood, however, that any of the disclosed devices may be operated in accordance with any suitable detection methodology, and that any disclosed method may be employed in the operation of any suitable device. Furthermore, the disclosed devices and methods are applicable in a wide variety of situations or modes of operation, including but not limited to invasive, noninvasive, intermittent or continuous measurement, subcutaneous implantation, wearable detection systems, or any combination thereof.

Any method which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the method(s) in question.

A. Noninvasive System

1. Monitor Structure

FIG. 1 depicts a noninvasive optical detection system (hereinafter "noninvasive system") 10 in a presently preferred configuration. The depicted noninvasive system 10 is particularly suited for noninvasively detecting the concentration of an analyte in a material sample S, by observing the infrared energy emitted by the sample, as will be discussed in further detail below.

As used herein, the term "noninvasive" is a broad term and is used in its ordinary sense and refers, without limitation, to analyte detection devices and methods which have the capability to determine the concentration of an analyte in in-vivo tissue samples or bodily fluids. It should be understood, however, that the noninvasive system 10 disclosed herein is not limited to noninvasive use, as the noninvasive system 10 may be employed to analyze an in-vitro fluid or tissue sample which has been obtained invasively or noninvasively. As used herein, the term "invasive" (or, alternatively, "traditional") is a broad term and is used in its ordinary sense and refers, without limitation, to analyte detection methods which involve the removal of fluid samples through the skin. As used herein, the term "material sample" is a broad term and is used in its ordinary sense and refers, without limitation, to any collection of material which is suitable for analysis by the noninvasive system 10. For example, the material sample S may comprise a tissue sample, such as a human forearm, placed against the noninvasive system 10. The material sample S may also comprise a volume of a bodily fluid, such as whole blood, blood component(s), interstitial fluid or intercellular fluid obtained invasively, or saliva or urine obtained noninvasively, or any collection of organic or inorganic material. As used herein, the term "analyte" is a broad term and is used in its ordinary sense and refers, without limitation, to any chemical species the presence or concentration of which is sought in the material sample S by the noninvasive system 10. For example, the analyte(s) which may be detected by the noninvasive system 10 include but not are limited to glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, electrolytes, sodium, potassium, chloride, bicarbonate, and hormones. As used herein to describe measurement techniques, the term "continuous" is a broad term and is used in its ordinary sense and refers, without limitation, to the taking of discrete measurements more frequently than about once every 10 minutes, and/or the taking of a stream or series of measurements or other data over any suitable time interval, for example, over an interval of one to several seconds, minutes, hours, days, or longer. As used herein to describe measurement techniques, the term "intermittent" is a broad term and is used in its ordinary sense and refers, without limitation, to the taking of measurements less frequently than about once every 10 minutes.

The noninvasive system 10 preferably comprises a window assembly 12, although in some embodiments the window assembly 12 may be omitted. One function of the window assembly 12 is to permit infrared energy E to enter the noninvasive system 10 from the sample S when it is placed against an upper surface 12a of the window assembly 12. The window assembly 12 includes a heater layer (see discussion below) which is employed to heat the material sample S and stimulate emission of infrared energy therefrom. A cooling system 14, preferably comprising a Peltier-type thermoelectric device, is in thermally conductive relation to the window assembly 12 so that the temperature of the window assembly 12 and the material sample S can be manipulated in accordance with a detection methodology discussed in greater detail below. The cooling system 14 includes a cold surface 14a which is in thermally conductive relation to a cold reservoir 16 and the window assembly 12, and a hot surface 14b which is in thermally conductive relation to a heat sink 18.

As the infrared energy E enters the noninvasive system 10, it first passes through the window assembly 12, then through an optical mixer 20, and then through a collimator 22. The optical mixer 20 preferably comprises a light pipe having highly reflective inner surfaces which randomize the directionality of the infrared energy E as it passes therethrough and reflects against the mixer walls. The collimator 22 also comprises a light pipe having highly-reflective inner walls, but the walls diverge as they extend away from the mixer 20. The divergent walls cause the infrared energy E to tend to straighten as it advances toward the wider end of the collimator 22, due to the angle of incidence of the infrared energy when reflecting against the collimator walls.

From the collimator 22 the infrared energy E passes through an array of filters 24, each of which allows only a selected wavelength or band of wavelengths to pass therethrough. These wavelengths/bands are selected to highlight or isolate the absorptive effects of the analyte of interest in the detection methodology discussed in greater detail below. Each filter 24 is preferably in optical communication with a concentrator 26 and an infrared detector 28. The concentrators 26 have highly reflective, converging inner walls which concentrate the infrared energy as it advances toward the detectors 28, increasing the density of the energy incident upon the detectors 28.

The detectors 28 are in electrical communication with a control system 30 which receives electrical signals from the detectors 28 and computes the concentration of the analyte in the sample S. The control system 30 is also in electrical communication with the window 12 and cooling system 14, so as to monitor the temperature of the window 12 and/or cooling system 14 and control the delivery of electrical power to the window 12 and cooling system 14.

a. Window Assembly

Figure 2:
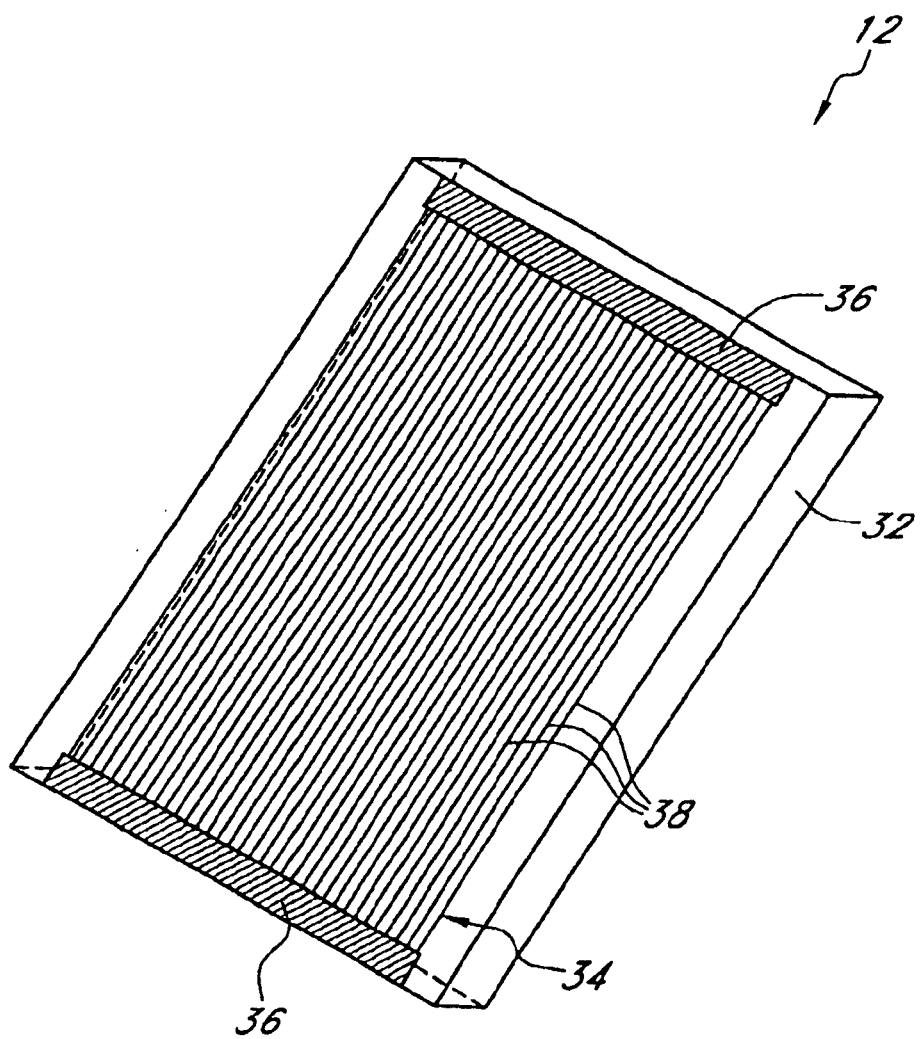
FIG. 2 is a perspective view of a window assembly for use with the noninvasive detection system.

A preferred configuration of the window assembly 12 is shown in perspective, as viewed from its underside (in other words, the side of the window assembly 12 opposite the sample S), in FIG. 2. The window assembly 12 generally comprises a main layer 32 formed of a highly infrared-transmissive material and a heater layer 34 affixed to the underside of the main layer 32. The main layer 32 is preferably formed from diamond, most preferably from chemical-vapor-deposited ("CVD") diamond, with a preferred thickness of about 0.25 millimeters. In other embodiments alternative materials which are highly infrared-transmissive, such as silicon or germanium, may be used in forming the main layer 32.

The heater layer 34 preferably comprises bus bars 36 located at opposing ends of an array of heater elements 38. The bus bars 36 are in electrical communication with the elements 38 so that, upon connection of the bus bars 36 to a suitable electrical power source (not shown) a current may be passed through the elements 38 to generate heat in the window assembly 12. The heater layer 34 may also include one or more temperature sensors (not shown), such as thermistors or resistance temperature devices (RTDs), to measure the temperature of the window assembly 12 and provide temperature feedback to the control system 30 (see FIG. 1).

Still referring to FIG. 2, the heater layer 34 preferably comprises a first adhesion layer of gold or platinum (hereinafter referred to as the "gold" layer) deposited over an alloy layer which is applied to the main layer 32. The alloy layer comprises a material suitable for implementation of the heater layer 34, such as, by way of example, 10/90 titanium/tungsten, titanium/platinum, nickel/chromium, or other similar material. The gold layer preferably has a thickness of about 4000 Å, and the alloy layer preferably has a thickness ranging between about 300 Å and about 500 Å. The gold layer and/or the alloy layer may be deposited onto the main layer 32 by chemical deposition including, but not necessarily limited to, vapor deposition, liquid deposition, plating, laminating, casting, sintering, or other forming or deposition methodologies well known to those or ordinary skill in the art. If desired, the heater layer 34 may be covered with an electrically insulating coating which also enhances adhesion to the main layer 32. One preferred coating material is aluminum oxide. Other acceptable materials include, but are not limited to, titanium dioxide or zinc selenide.

The heater layer 34 may incorporate a variable pitch distance between centerlines of adjacent heater elements 38 to maintain a constant power density, and promote a uniform temperature, across the entire layer 34. Where a constant pitch distance is employed, the preferred distance is at least about 50–100 microns. Although the heater elements 38 generally have a preferred width of about 25 microns, their width may also be varied as needed for the same reasons stated above.

Alternative structures suitable for use as the heater layer 34 include, but are not limited to, thermoelectric heaters, radiofrequency (RF) heaters, infrared radiation heaters, optical heaters, heat exchangers, electrical resistance heating grids, wire bridge heating grids, or laser heaters. Whichever type of heater layer is employed, it is preferred that the heater layer obscures about 10% or less of the window assembly 12.

In a preferred embodiment, the window assembly 12 comprises substantially only the main layer 32 and the heater layer 34. Thus, when installed in an optical detection system such as the noninvasive system 10 shown in FIG. 1, the window assembly 12 will facilitate a minimally obstructed optical path between a (preferably flat) upper surface 12a of the window assembly 12 and the infrared detectors 28 of the noninvasive system 10. The optical path 32 in the preferred noninvasive system 10 proceeds only through the main layer 32 and heater layer 34 of the window assembly 12 (including any antireflective, index-matching, electrical insulating or protective coatings applied thereto or placed therein), through the optical mixer 20 and collimator 22 and to the detectors 28.

Figure 2A:
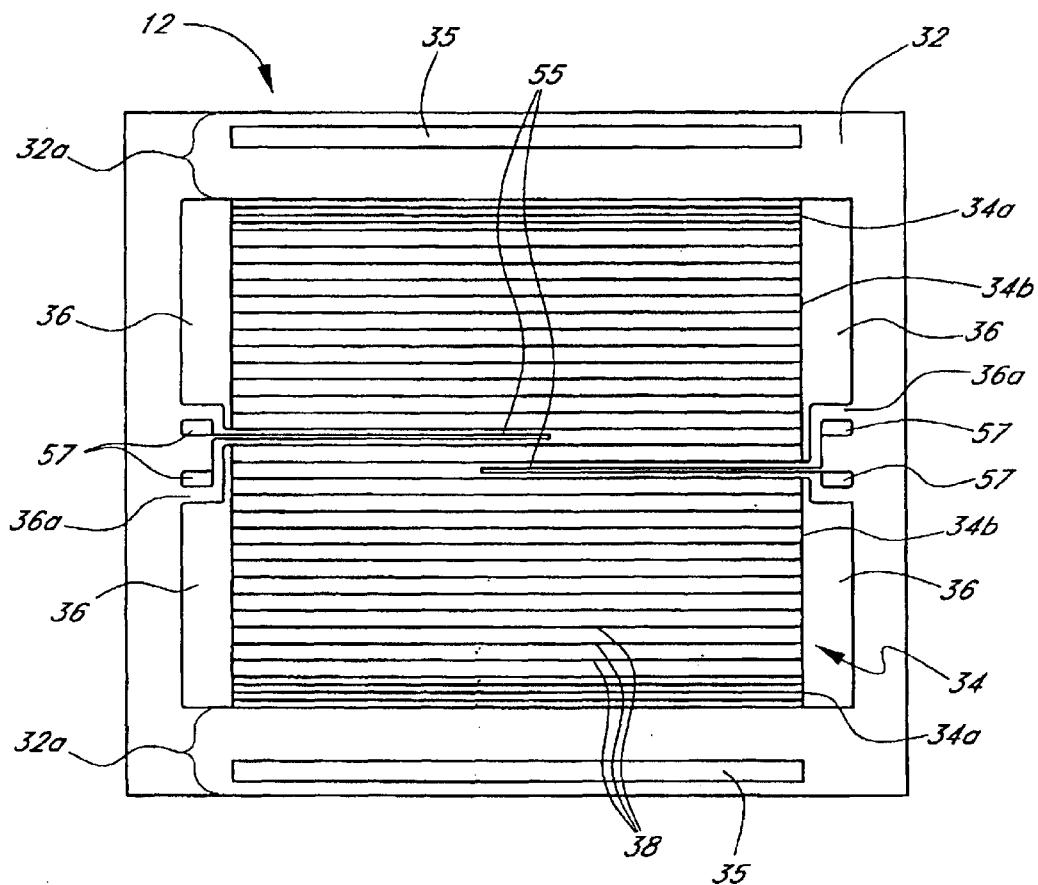
FIG. 2A is a plan view of another embodiment of a window assembly for use with the noninvasive detection system.

FIG. 2A shows another embodiment of the window assembly 12, that may be used in place of the window assembly 12 depicted in FIG. 2. The window assembly 12 shown in FIG. 2A may be similar to that shown in FIG. 2, except as described below. In the embodiment of FIG. 2A the main layer 32 has a preferred thickness of up to about 0.012" and more preferably about 0.010" or less. The heater layer 34 may also include one or more resistance temperature devices (RTD's) 55 to measure the temperature of the window assembly 12 and provide temperature feedback to a control system 30. The RTDs 55 terminate in RTD connection pads 57.

Figure 6:
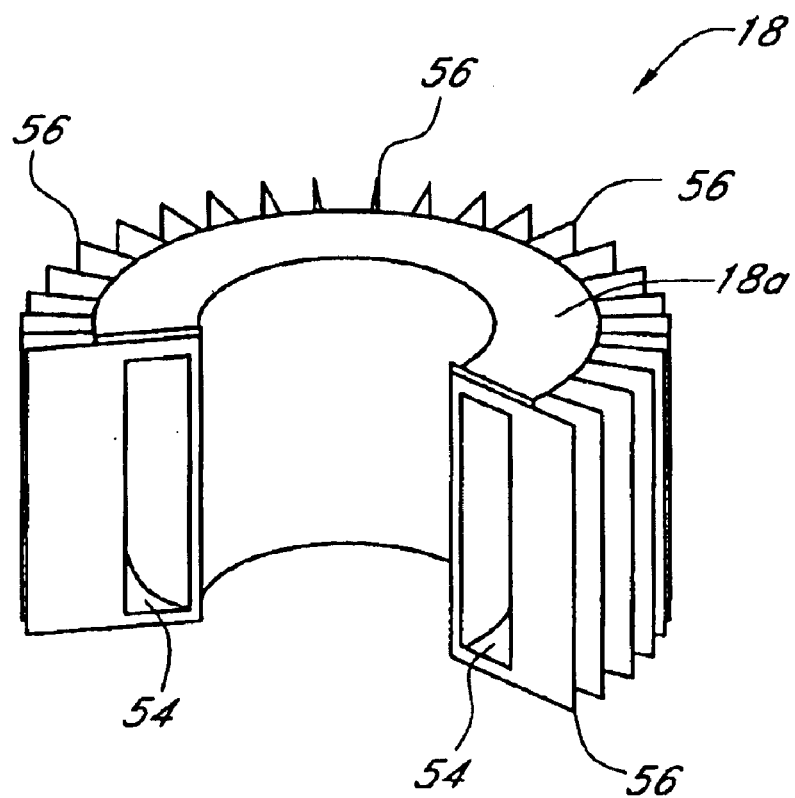
FIG. 6 is a cutaway view of a heat sink for use with the noninvasive detection system.

In the embodiment of FIG. 2A, the heater elements 38 are typically provided with a width of about 25 microns. The pitch distance separating centerlines of adjacent heater elements 38 may be reduced, and/or the width of the heater elements 38 may be increased, in the regions of the window assembly 12 near the point(s) of contact with the thermal diffuser 410 (see FIGS. 6B–6D and discussion below). This arrangement advantageously promotes an isothermal temperature profile at the upper surface of the main layer 32 despite thermal contact with the thermal diffuser.

The embodiment shown in FIG. 2A includes a plurality of heater elements 38 of substantially equal width which are variably spaced across the width of the main layer 32. In the embodiment of FIG. 2A, the centerlines of the heater elements 38 are spaced at a first pitch distance of about 0.0070" at peripheral portions 34a of the heater layer 34, and at a second pitch distance of about 0.015" at a central portion 34b of the main layer 32. The heater elements 38 closest to the center are preferably sufficiently spaced to allow the RTDs 55 to extend therebetween. In the embodiment of FIG. 2A, the main layer 32 includes peripheral regions 32a which extend about 0.053" from the outermost heater element on each side of the heater layer 34 to the adjacent edge of the main layer 32. As shown, the bus bars 36 are preferably configured and segmented to allow space for the RTDs 55 and the RTD connection pads 57, in intermediate gaps 36a.

The RTDs 55 preferably extend into the array of heater elements 38 by distance that is slightly longer than half of the length of an individual heater element 38. In alternative embodiments, the RTDs 55 may be located at the edges of the main layer 32, or at other locations as desired for a particular noninvasive system.

With continued reference to FIG. 2A, the peripheral regions of the main layer 32 may include metallized edge portions 35 for facilitating connection to the diffuser 410 (discussed below in connection with FIGS. 6B–6D). The metallized edge portions 35 may be formed by the same or similar processes used in forming the heater elements 38 and RTDs 55. In the embodiment of FIG. 2A, the edge portions 35 are typically between about 0.040" and about 0.060" wide by about 0.450" and about 0.650" long, and in one embodiment, they are about 0.050" by about 0.550". Other dimensions may be appropriately used so long as the window assembly 12 may be joined in thermal communication with the diffuser 410 as needed.

In the embodiment shown in FIG. 2A, the main layer 32 is about 0.690" long by about 0.571" wide, and the heater layer (excluding the metallized edge portions 35) is about 0.640" long by about 0.465" wide. The main layer 32 is about 0.010"–0.012" thick, and is advantageously thinner than about 0.010" where possible. Each heater element 38 is about 0.570" long, and each peripheral region 34a is about 0.280" wide. These dimensions are merely exemplary; of course, other dimensions may be used as desired.

Figure 3:
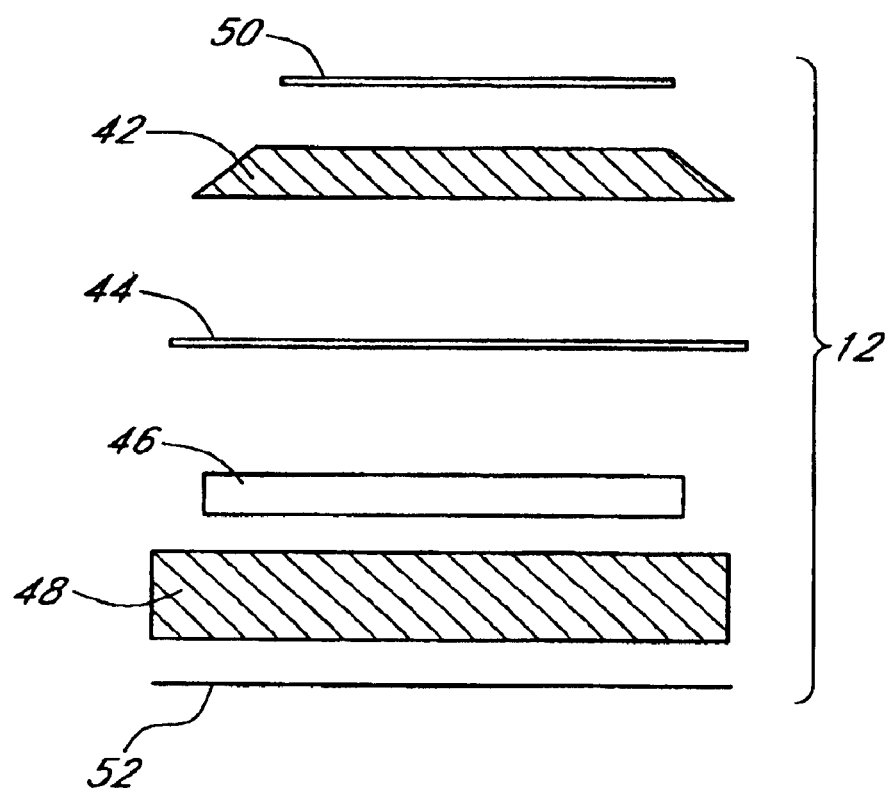
FIG. 3 is an exploded schematic view of another embodiment of a window assembly for use with the noninvasive detection system.

FIG. 3 depicts an exploded side view of an alternative configuration for the window assembly 12, which may be used in place of the configuration shown in FIG. 2. The window assembly 12 depicted in FIG. 3 includes near its upper surface (the surface intended for contact with the sample S) a highly infrared-transmissive, thermally conductive spreader layer 42. Underlying the spreader layer 42 is a heater layer 44. A thin electrically insulating layer (not shown), such as layer of aluminum oxide, titanium dioxide or zinc selenide, may be disposed between the heater layer 44 and the spreader layer 42. (An aluminum oxide layer also increases adhesion of the heater layer 44 to the spreader layer 42.) Adjacent to the heater layer 44 is a thermal insulating and impedance matching layer 46. Adjacent to the thermal insulating layer 46 is a thermally conductive inner layer 48. The spreader layer 42 is coated on its top surface with a thin layer of protective coating 50. The bottom surface of the inner layer 48 is coated with a thin overcoat layer 52. Preferably, the protective coating 50 and the overcoat layer 52 have antireflective properties.

The spreader layer 42 is preferably formed of a highly infrared-transmissive material having a high thermal conductivity sufficient to facilitate heat transfer from the heater layer 44 uniformly into the material sample S when it is placed against the window assembly 12. Other effective materials include, but are not limited to, CVD diamond, diamondlike carbon, gallium arsenide, germanium, and other infrared-transmissive materials having sufficiently high thermal conductivity. Preferred dimensions for the spreader layer 42 are about one inch in diameter and about 0.010 inch thick. As shown in FIG. 3, a preferred embodiment of the spreader layer 42 incorporates a beveled edge. Although not required, an approximate 45-degree bevel is preferred.

The protective layer 50 is intended to protect the top surface of the spreader layer 42 from damage. Ideally, the protective layer is highly infrared-transmissive and highly resistant to mechanical damage, such as scratching or abrasion. It is also preferred that the protective layer 50 and the overcoat layer 52 have high thermal conductivity and antireflective and/or index-matching properties. A satisfactory material for use as the protective layer 50 and the overcoat layer 52 is the multi-layer Broad Band Anti-Reflective Coating produced by Deposition Research Laboratories, Inc. of St. Charles, Mo. Diamondlike carbon coatings are also suitable.

Except as noted below, the heater layer 44 is generally similar to the heater layer 34 employed in the window assembly shown in FIG. 2. Alternatively, the heater layer 44 may comprise a doped infrared-transmissive material, such as a doped silicon layer, with regions of higher and lower resistivity. The heater layer 44 preferably has a resistance of about 2 ohms and has a preferred thickness of about 1,500 angstroms. A preferred material for forming the heater layer 44 is a gold alloy, but other acceptable materials include, but are not limited to, platinum, titanium, tungsten, copper, and nickel.

The thermal insulating layer 46 prevents the dissipation of heat from the heater element 44 while allowing the cooling system 14 to effectively cool the material sample S (see FIG. 1). This layer 46 comprises a material having thermally insulative (e.g., lower thermal conductivity than the spreader layer 42) and infrared transmissive qualities. A preferred material is a germanium-arsenic-selenium compound of the calcogenide glass family known as AMTIR-1 produced by Amorphous Materials, Inc. of Garland, Tex. The pictured embodiment has a diameter of about 0.85 inches and a preferred thickness in the range of about 0.005 to about 0.010 inches. As heat generated by the heater layer 44 passes through the spreader layer 42 into the material sample S, the thermal insulating layer 46 insulates this heat.

The inner layer 48 is formed of thermally conductive material, preferably crystalline silicon formed using a conventional floatzone crystal growth method. The purpose of the inner layer 48 is to serve as a cold-conducting mechanical base for the entire layered window assembly.

The overall optical transmission of the window assembly 12 shown in FIG. 3 is preferably at least 70%. The window assembly 12 of FIG. 3 is preferably held together and secured to the noninvasive system 10 by a holding bracket (not shown). The bracket is preferably formed of a glass-filled plastic, for example Ultem 2300, manufactured by General Electric. Ultem 2300 has low thermal conductivity which prevents heat transfer from the layered window assembly 12.

b. Cooling System

The cooling system 14 (see FIG. 1) preferably comprises a Peltier-type thermoelectric device. Thus, the application of an electrical current to the preferred cooling system 14 causes the cold surface 14a to cool and causes the opposing hot surface 14b to heat up. The cooling system 14 cools the window assembly 12 via the situation of the window assembly 12 in thermally conductive relation to the cold surface 14a of the cooling system 14. It is contemplated that the cooling system 14, the heater layer 34, or both, can be operated to induce a desired time-varying temperature in the window assembly 12 to create an oscillating thermal gradient in the sample S, in accordance with various analyte-detection methodologies discussed herein.

Preferably, the cold reservoir 16 is positioned between the cooling system 14 and the window assembly 12, and functions as a thermal conductor between the system 14 and the window assembly 12. The cold reservoir 16 is formed from a suitable thermally conductive material, preferably brass. Alternatively, the window assembly 12 can be situated in direct contact with the cold surface 14a of the cooling system 14.

In alternative embodiments, the cooling system 14 may comprise a heat exchanger through which a coolant, such as air, nitrogen or chilled water, is pumped, or a passive conduction cooler such as a heat sink. As a further alternative, a gas coolant such as nitrogen may be circulated through the interior of the noninvasive system 10 so as to contact the underside of the window assembly 12 (see FIG. 1) and conduct heat therefrom.

Figure 4:
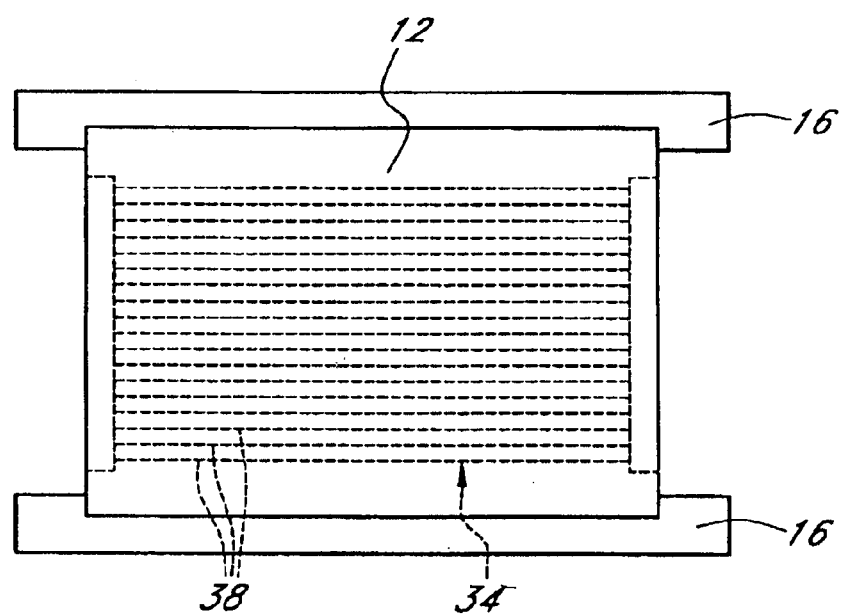
FIG. 4 is a plan view of the window assembly connected to a cooling system.
Figure 5:
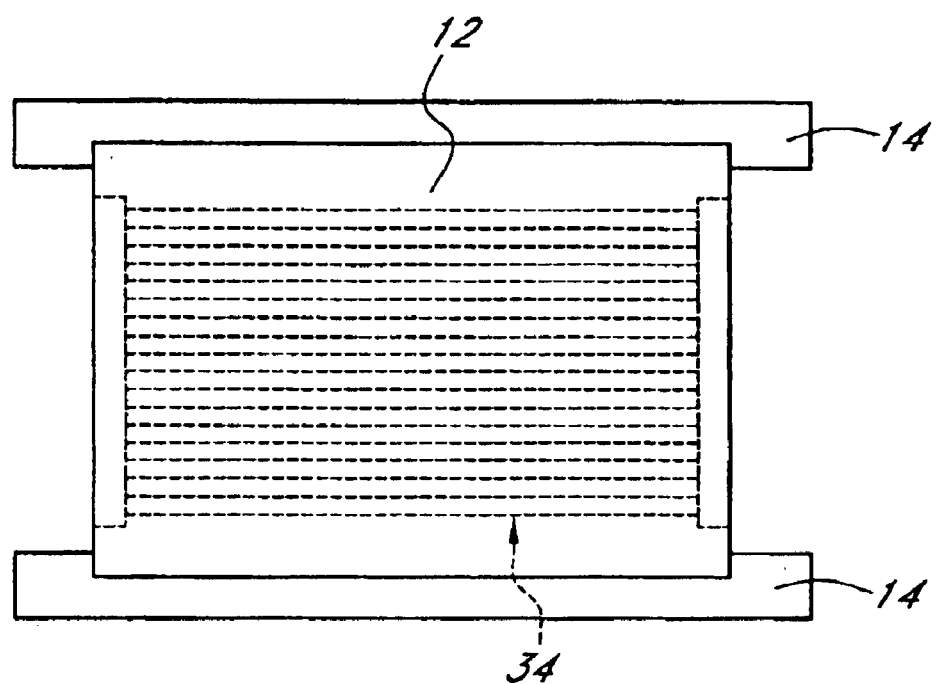
FIG. 5 is a plan view of the window assembly connected to a cold reservoir.

FIG. 4 is a top schematic view of a preferred arrangement of the window assembly 12 (of the types shown in FIG. 2 or 2A) and the cold reservoir 16, and FIG. 5 is a top schematic view of an alternative arrangement in which the window assembly 12 directly contacts the cooling system 14. The cold reservoir 16/cooling system 14 preferably contacts the underside of the window assembly 12 along opposing edges thereof, on either side of the heater layer 34. With thermal conductivity thus established between the window assembly 12 and the cooling system 14, the window assembly can be cooled as needed during operation of the noninvasive system 10. In order to promote a substantially uniform or isothermal temperature profile over the upper surface of the window assembly 12, the pitch distance between centerlines of adjacent heater elements 38 may be made smaller (thereby increasing the density of heater elements 38) near the region(s) of contact between the window assembly 12 and the cold reservoir 16/cooling system 14. As a supplement or alternative, the heater elements 38 themselves may be made wider near these regions of contact. As used herein, "isothermal" is a broad term and is used in its ordinary sense and refers, without limitation, to a condition in which, at a given point in time, the temperature of the window assembly 12 or other structure is substantially uniform across a surface intended for placement in thermally conductive relation to the material sample S. Thus, although the temperature of the structure or surface may fluctuate over time, at any given point in time the structure or surface may nonetheless be isothermal.

The heat sink 18 drains waste heat from the hot surface 14b of the cooling system 16 and stabilizes the operational temperature of the noninvasive system 10. The preferred heat sink 18 (see FIG. 6) comprises a hollow structure formed from brass or any other suitable material having a relatively high specific heat and high heat conductivity. The heat sink 18 has a conduction surface 18a which, when the heat sink 18 is installed in the noninvasive system 18, is in thermally conductive relation to the hot surface 14b of the cooling system 14 (see FIG. 1). A cavity 54 is formed in the heat sink 18 and preferably contains a phase-change material (not shown) to increase the capacity of the sink 18. A preferred phase change material is a hydrated salt, such as calciumchloride hexahydrate, available under the name TH29 from PCM Thermal Solutions, Inc., of Naperville, Ill. Alternatively, the cavity 54 may be omitted to create a heat sink 18 comprising a solid, unitary mass. The heat sink 18 also forms a number of fins 56 to further increase the conduction of heat from the sink 18 to surrounding air.

Alternatively, the heat sink 18 may be formed integrally with the optical mixer 20 and/or the collimator 22 as a unitary mass of rigid, heat-conductive material such as brass or aluminum. In such a heat sink, the mixer 20 and/or collimator 22 extend axially through the heat sink 18, and the heat sink defines the inner walls of the mixer 20 and/or collimator 22. These inner walls are coated and/or polished to have appropriate reflectivity and nonabsorbance in infrared wavelengths as will be further described below. Where such a unitary heat sink-mixer-collimator is employed, it is desirable to thermally insulate the detector array from the heat sink.

It should be understood that any suitable structure may be employed to heat and/or cool the material sample S, instead of or in addition to the window assembly 12/cooling system 14 disclosed above, so long a proper degree of cycled heating and/or cooling are imparted to the material sample S. In addition other forms of energy, such as but not limited to light, radiation, chemically induced heat, friction and vibration, may be employed to heat the material sample S. It will be further appreciated that heating of the sample can achieved by any suitable method, such as convection, conduction, radiation, etc.

c. Window Mounting System

FIG. 6B illustrates an exploded view of a window mounting system 400 which, in one embodiment, is employed as part of the noninvasive system 10 disclosed above. Where employed in connection with the noninvasive system 10, the window mounting system 400 supplements or, where appropriate, replaces any of the window assembly 12, cooling system 14, cold reservoir 16 and heat sink 18 shown in FIG. 1. In one embodiment, the window mounting system 400 is employed in conjunction with the window assembly 12 depicted in FIG. 2A; in alternative embodiments, the window assemblies shown in FIGS. 2 and 3 and described above may also be used in conjunction with the window mounting system 400 illustrated in FIG. 6B.

In the window mounting system 400, the window assembly 12 is physically and electrically connected (typically by soldering) to a first printed circuit board ("first PCB") 402. The window assembly 12 is also in thermally conductive relation (typically by contact) to a thermal diffuser 410. The window assembly may also be fixed to the diffuser 410 by soldering.

The thermal diffuser 410 generally comprises a heat spreader layer 412 which, as mentioned, preferably contacts the window assembly 12, and a conductive layer 414 which is typically soldered to the heat spreader layer 412. The conductive layer 414 may then be placed in direct contact with a cold side 418a of a thermoelectric cooler (TEC) 418 or other cooling device. The TEC 418, which in one embodiment comprises a 25 W TEC manufactured by MELCOR, is in electrical communication with a second PCB 403, which includes TEC power leads 409 and TEC power terminals 411 for connection of the TEC 418 to an appropriate power source (not shown). The second PCB 403 also includes contacts 408 for connection with RTD terminals 407 (see FIG. 6C) of the first PCB 402. A heat sink 419, which may take the form of the illustrated water jacket, the heat sink 18 shown in FIG. 6, any other heat sink structures mentioned herein, or any other appropriate device, is in thermal communication with a hot side 418b of the TEC 418 (or other cooling device), in order to remove any excess heat created by the TEC 418.

Figure 6A:
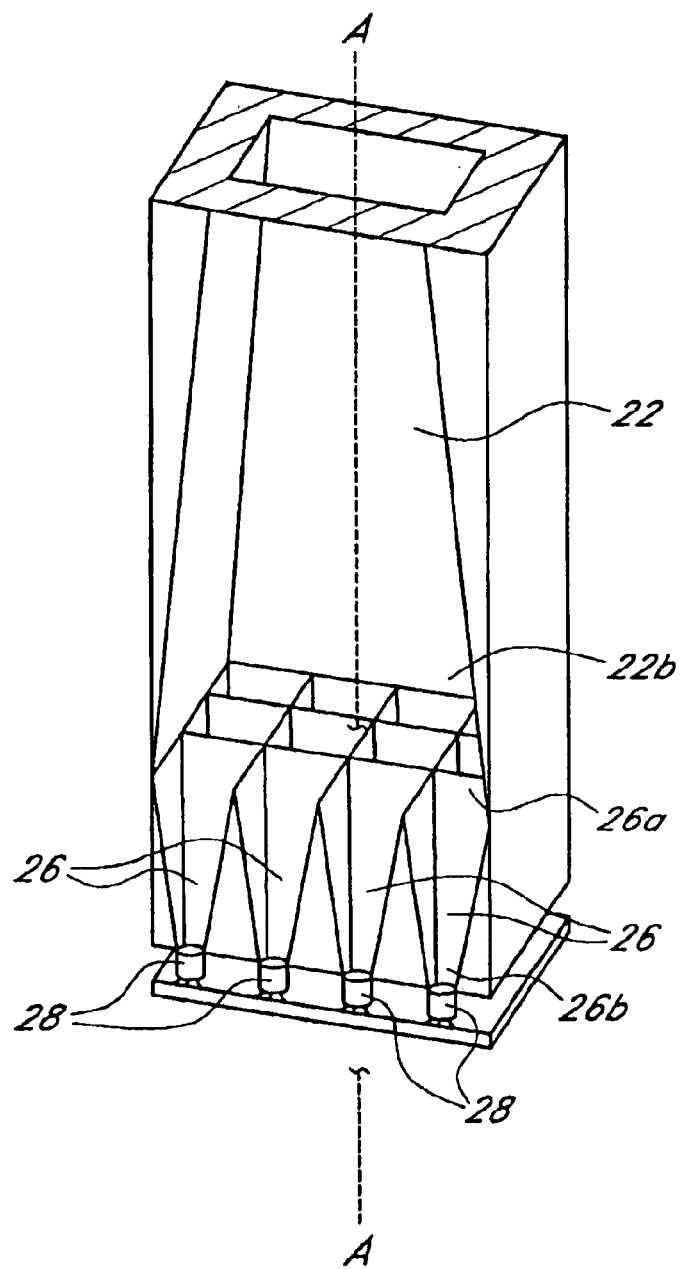
FIG. 6A is a cutaway perspective view of a lower portion of the noninvasive detection system of FIG. 1.
Figure 6C:
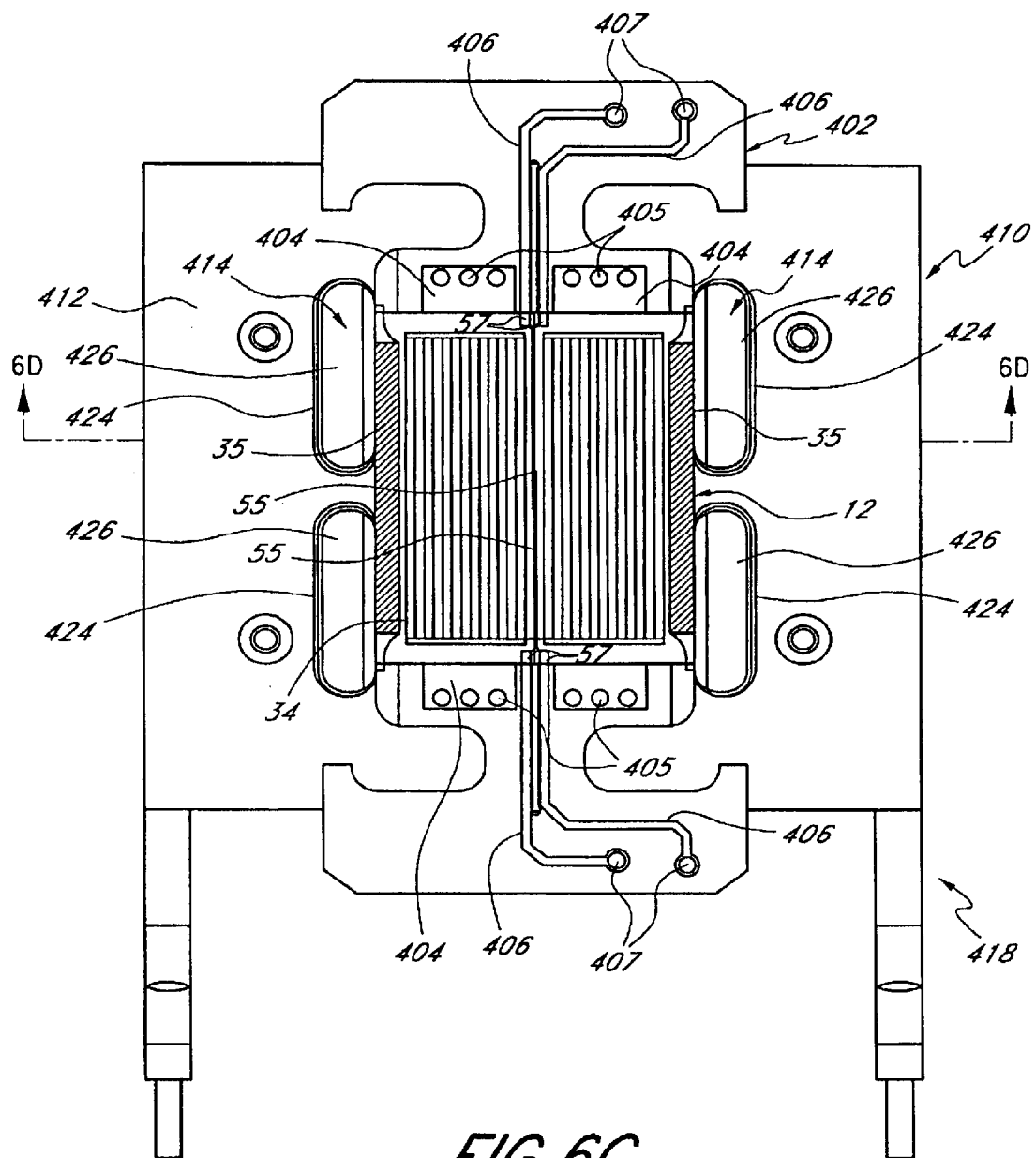
FIG. 6C is a partial plan view of the window mounting system of FIG. 6B.

FIG. 6C illustrates a plan view of the interconnection of the window assembly 12, the first PCB 402, the diffuser 410 and the thermoelectric cooler 418. The first PCB includes RTD bonding leads 406 and heater bonding pads 404 which permit attachment of the RTDs 55 and bus bars 36, respectively, of the window assembly 12 to the first PCB 402 via soldering or other conventional techniques. Electrical communication is thus established between the heater elements 38 of the heater layer 34, and heater terminals 405 formed in the heater bonding pads 404. Similarly, electrical communication is established between the RTDs 55 and RTD terminals 407 formed at the ends of the RTD bonding leads 406. Electrical connections can be established with the heater elements 38 and the RTDs 55 via simple connection to the terminals 405, 407 of the first PCB 402.

With further reference to FIGS. 2A and 6B–6C, the heat spreader layer 412 of the thermal diffuser 410 contacts the underside of the main layer 32 of the window assembly 12 via a pair of rails 416. The rails 416 may contact the main layer 32 at the metallized edge portions 35, or at any other appropriate location. The physical and thermal connection between the rails 416 and the window main layer 32 may be achieved by soldering, as indicated above. Alternatively, the connection may be achieved by an adhesive such as epoxy, or any other appropriate method. The material chosen for the window main layer 32 is preferably sufficiently thermally conductive that heat may be quickly removed from the main layer 32 through the rails 416, the diffuser 410, and the TEC 128.

Figure 6D:
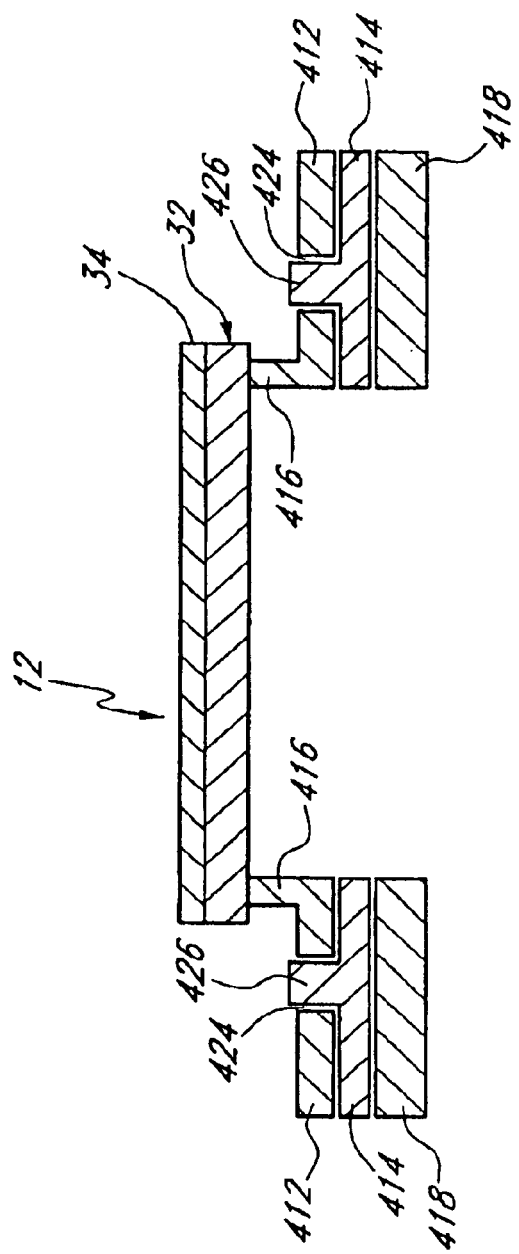
FIG. 6D is a sectional view of the window mounting system of FIG. 6C.

FIG. 6D shows a cross-sectional view of the assembly of FIG. 6C through line 22—22. As can be seen in FIG. 6D, the window assembly 12 contacts the rails 416 of the heat spreader layer 412. The conductive layer 414 underlies the spreader layer 412 and may comprise protrusions 426 configured to extend through openings 424 formed in the spreader layer 412. The openings 424 and protrusions 426 are sized to leave sufficient expansion space therebetween, to allow expansion and contraction of the conductive layer 414 without interference with, or causing deformation of, the window assembly 12 or the heat spreader layer 412. Moreover, the protrusions 426 and openings 424 coact to prevent displacement of the spreader layer 412 with respect to the conductive layer 414 as the conductive layer 414 expands and contracts.

The thermal diffuser 410 provides a thermal impedance between the TEC 418 and the window assembly 12, which impedance is selected to drain heat from the window assembly at a rate proportional to the power output of the heater layer 34. In this way, the temperature of the main layer 32 can be rapidly cycled between a "hot" and a "cold" temperatures, thereby allowing a time-varying thermal gradient to be induced in a sample S placed against the window assembly 12.

The heat spreader layer 412 is preferably made of a material which has substantially the same coefficient of thermal expansion as the material used to form the window assembly main layer 32, within the expected operating temperature range. Preferably, both the material used to form the main layer 32 and the material used to form the heat spreader layer 412 have substantially the same, extremely low, coefficient of thermal expansion. For this reason, CVD diamond is preferred for the main layer 32 (as mentioned above); with a CVD diamond main layer 32 the preferred material for the heat spreader layer 412 is Invar. Invar advantageously has an extremely low coefficient of thermal expansion and a relatively high thermal conductivity. Because Invar is a metal, the main layer 32 and the heat spreader layer 412 can be thermally bonded to one another with little difficulty. Alternatively, other materials may be used for the heat spreader layer 412; for example, any of a number of glass and ceramic materials with low coefficients of thermal expansion may be employed.

The conductive layer 414 of the thermal diffuser 410 is typically a highly thermally conductive material such as copper (or, alternatively, other metals or non-metals exhibiting comparable thermal conductivities). The conductive layer 414 is typically soldered or otherwise bonded to the underside of the heat spreader layer 412.

In the illustrated embodiment, the heat spreader layer 412 may be constructed according to the following dimensions, which are to be understood as exemplary; accordingly the dimensions may be varied as desired. The heat spreader layer 412 has an overall length and width of about 1.170", with a central opening of about 0.590" long by 0.470" wide. Generally, the heat spreader layer 412 is about 0.030" thick; however, the rails 416 extend a further 0.045" above the basic thickness of the heat spreader layer 412. Each rail 416 has an overall length of about 0.710"; over the central 0.525" of this length each rail 416 is about 0.053" wide. On either side of the central width each rail 416 tapers, at a radius of about 0.6", down to a width of about 0.023". Each opening 424 is about 0.360" long by about 0.085" wide, with corners rounded at a radius of about 0.033".

In the illustrated embodiment, conductive layer 414 may be constructed according to the following dimensions, which are to be understood as exemplary; accordingly the dimensions may be varied as desired. The conductive layer 414 has an overall length and width of about 1.170", with a central opening of about 0.590" long by 0.470" wide. Generally, the conductive layer 412 is about 0.035" thick; however, the protrusions 426 extend a further 0.075"–0.085" above the basic thickness of the conductive layer 414. Each protrusion 426 is about 0.343" long by about 0.076" wide, with corners rounded at a radius of about 0.035".

As shown in FIG. 6B, first and second clamping plates 450 and 452 may be used to clamp the portions of the window mounting system 400 to one another. For example, the second clamping plate 452 is configured to clamp the window assembly 12 and the first PCB 402 to the diffuser 410 with screws or other fasteners extending through the openings shown in the second clamping plate 452, the heat spreader layer 412 and the conductive layer 414. Similarly, the first clamping plate 450 is configured overlie the second clamping plate 452 and clamp the rest of the window mounting system 400 to the heat sink 419, thus sandwiching the second clamping plate 452, the window assembly 12, the first PCB 402, the diffuser 410, the second PCB 403, and the TEC 418 therebetween. The first clamping plate 450 prevents undesired contact between the sample S and any portion of the window mounting system 400, other than the window assembly 12 itself. Other mounting plates and mechanisms may also be used as desired.

d. Optics

As shown in FIG. 1, the optical mixer 20 comprises a light pipe with an inner surface coating which is highly reflective and minimally absorptive in infrared wavelengths, preferably a polished gold coating, although other suitable coatings may be used where other wavelengths of electromagnetic radiation are employed. The pipe itself may be fabricated from a another rigid material such as aluminum or stainless steel, as long as the inner surfaces are coated or otherwise treated to be highly reflective. Preferably, the optical mixer 20 has a rectangular cross-section (as taken orthogonal to the longitudinal axis A—A of the mixer 20 and the collimator 22), although other cross-sectional shapes, such as other polygonal shapes or circular or elliptical shapes, may be employed in alternative embodiments. The inner walls of the optical mixer 20 are substantially parallel to the longitudinal axis A—A of the mixer 20 and the collimator 22. The highly reflective and substantially parallel inner walls of the mixer 20 maximize the number of times the infrared energy E will be reflected between the walls of the mixer 20, thoroughly mixing the infrared energy E as it propagates through the mixer 20. In a presently preferred embodiment, the mixer 20 is about 1.2 inches to 2.4 inches in length and its cross-section is a rectangle of about 0.4 inches by about 0.6 inches. Of course, other dimensions may be employed in constructing the mixer 20. In particular it is be advantageous to miniaturize the mixer or otherwise make it as small as possible Still referring to FIG. 1, the collimator 22 comprises a tube with an inner surface coating which is highly reflective and minimally absorptive in infrared wavelengths, preferably a polished gold coating. The tube itself may be fabricated from a another rigid material such as aluminum, nickel or stainless steel, as long as the inner surfaces are coated or otherwise treated to be highly reflective. Preferably, the collimator 22 has a rectangular cross-section, although other cross-sectional shapes, such as other polygonal shapes or circular, parabolic or elliptical shapes, may be employed in alternative embodiments. The inner walls of the collimator 22 diverge as they extend away from the mixer 20. Preferably, the inner walls of the collimator 22 are substantially straight and form an angle of about 7 degrees with respect to the longitudinal axis A—A. The collimator 22 aligns the infrared energy E to propagate in a direction that is generally parallel to the longitudinal axis A—A of the mixer 20 and the collimator 22, so that the infrared energy E will strike the surface of the filters 24 at an angle as close to 90 degrees as possible.

In a presently preferred embodiment, the collimator is about 7.5 inches in length. At its narrow end 22a, the cross-section of the collimator 22 is a rectangle of about 0.4 inches by 0.6 inches. At its wide end 22b, the collimator 22 has a rectangular cross-section of about 1.8 inches by 2.6 inches. Preferably, the collimator 22 aligns the infrared energy E to an angle of incidence (with respect to the longitudinal axis A—A) of about 0–15 degrees before the energy E impinges upon the filters 24. Of course, other dimensions or incidence angles may be employed in constructing and operating the collimator 22.

With further reference to FIGS. 1 and 6A, each concentrator 26 comprises a tapered surface oriented such that its wide end 26a is adapted to receive the infrared energy exiting the corresponding filter 24, and such that its narrow end 26b is adjacent to the corresponding detector 28. The inward-facing surfaces of the concentrators 26 have an inner surface coating which is highly reflective and minimally absorptive in infrared wavelengths, preferably a polished gold coating. The concentrators 26 themselves may be fabricated from a another rigid material such as aluminum, nickel or stainless steel, so long as their inner surfaces are coated or otherwise treated to be highly reflective. Preferably, the concentrators 26 have a rectangular cross-section (as taken orthogonal to the longitudinal axis A—A), although other cross-sectional shapes, such as other polygonal shapes or circular, parabolic or elliptical shapes, may be employed in alternative embodiments. The inner walls of the concentrators converge as they extend toward the narrow end 26b. Preferably, the inner walls of the collimators 26 are substantially straight and form an angle of about 8 degrees with respect to the longitudinal axis A—A. Such a configuration is adapted to concentrate infrared energy as it passes through the concentrators 26 from the wide end 26a to the narrow end 26b, before reaching the detectors 28.

In a presently preferred embodiment, each concentrator 26 is about 1.5 inches in length. At the wide end 26a, the cross-section of each concentrator 26 is a rectangle of about 0.6 inches by 0.57 inches. At the narrow end 26b, each concentrator 26 has a rectangular cross-section of about 0.177 inches by 0.177 inches. Of course, other dimensions or incidence angles may be employed in constructing the concentrators 26.

e. Filters

The filters 24 preferably comprise standard interference-type infrared filters, widely available from manufacturers such as Optical Coating Laboratory, Inc. ("OCLI") of Santa Rosa, Calif. In the embodiment illustrated in FIG. 1, a 3×4 array of filters 24 is positioned above a 3×4 array of detectors 28 and concentrators 26. As employed in this embodiment, the filters 24 are arranged in four groups of three filters having the same wavelength sensitivity. These four groups have bandpass center wavelengths of 7.15 $\mu$m±0.03 $\mu$m, 8.40 $\mu$m±0.03 $\mu$m, 9.48 $\mu$m±0.04 $\mu$m, and 11.10 $\mu$m±0.04 $\mu$m, respectively, which correspond to wavelengths around which water and glucose absorb electromagnetic radiation. Typical bandwidths for these filters range from 0.20 $\mu$m to 0.50 $\mu$m.

In an alternative embodiment, the array of wavelength-specific filters 24 may be replaced with a single Fabry-Perot interferometer, which can provide wavelength sensitivity which varies as a sample of infrared energy is taken from the material sample S. Thus, this embodiment permits the use of only one detector 28, the output signal of which varies in wavelength specificity over time. The output signal can be de-multiplexed based on the wavelength sensitivities induced by the Fabry-Perot interferometer, to provide a multiple-wavelength profile of the infrared energy emitted by the material sample S. In this embodiment, the optical mixer 20 may be omitted, as only one detector 28 need be employed.

In still other embodiments, the array of filters 24 may comprise a filter wheel that rotates different filters with varying wavelength sensitivities over a single detector 24. Alternatively, an electronically tunable infrared filter may be employed in a manner similar to the Fabry-Perot interferometer discussed above, to provide wavelength sensitivity which varies during the detection process. In either of these embodiments, the optical mixer 20 may be omitted, as only one detector 28 need be employed.

f. Detectors

The detectors 28 may comprise any detector type suitable for sensing infrared energy, preferably in the mid-infrared wavelengths. For example, the detectors 28 may comprise mercury-cadmium-telluride (MCT) detectors. A detector such as a Fermionics (Simi Valley, Calif.) model PV-9.1 with a PVA481-1 pre-amplifier is acceptable. Similar units from other manufacturers such as Graseby (Tampa, Fla.) can be substituted. Other suitable components for use as the detectors 28 include pyroelectric detectors, thermopiles, bolometers, silicon microbolometers and lead-salt focal plane arrays.

g. Control System

Figure 7:
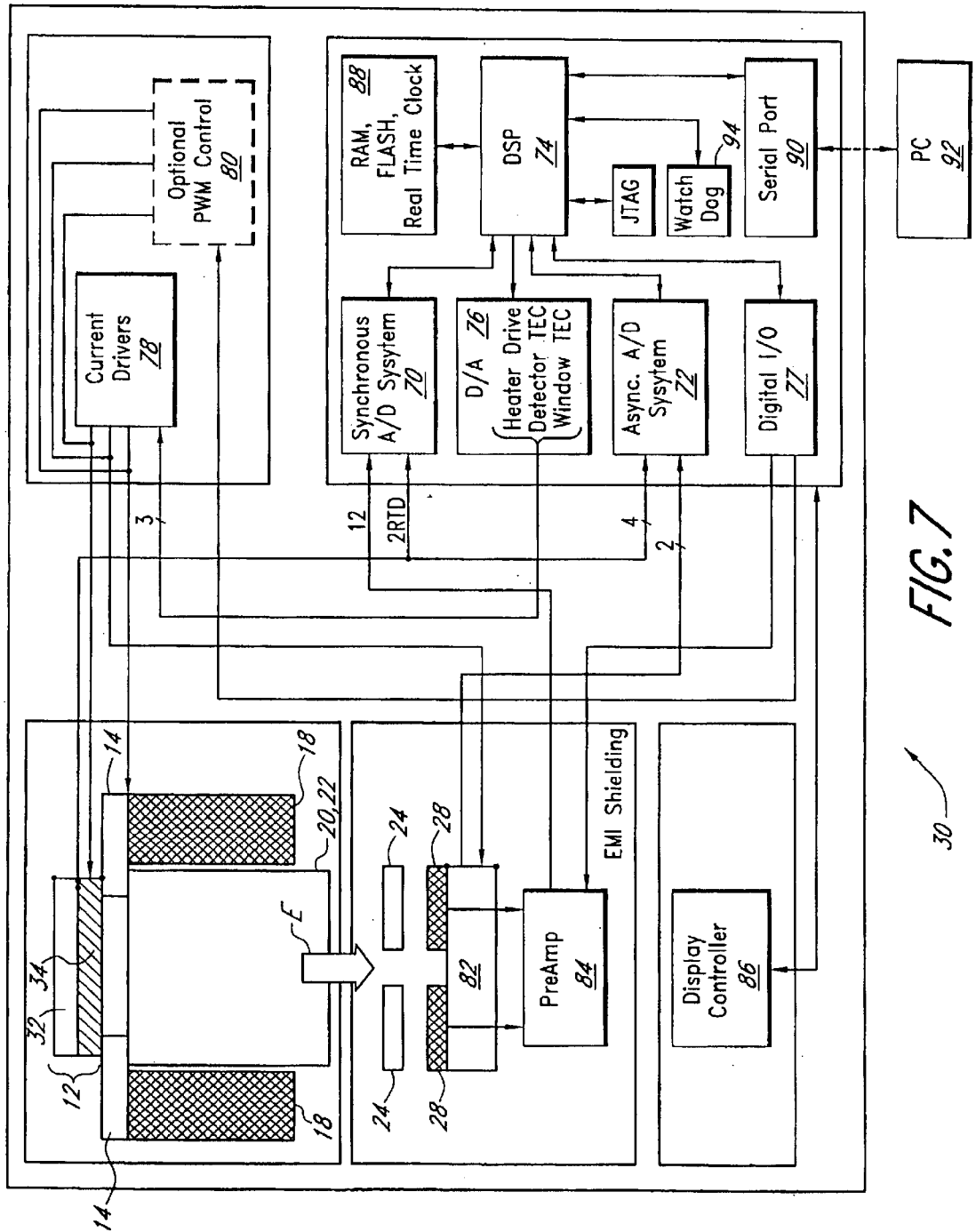
FIG. 7 is a schematic view of a control system for use with the noninvasive optical detection system.

FIG. 7 depicts the control system 30 in greater detail, as well as the interconnections between the control system and other relevant portions of the noninvasive system. The control system includes a temperature control subsystem and a data acquisition subsystem.

In the temperature control subsystem, temperature sensors (such as RTDs and/or thermistors) located in the window assembly 12 provide a window temperature signal to a synchronous analog-to-digital conversion system 70 and an asynchronous analog-to-digital conversion system 72. The A/D systems 70, 72 in turn provide a digital window temperature signal to a digital signal processor (DSP) 74. The processor 74 executes a window temperature control algorithm and determines appropriate control inputs for the heater layer 34 of the window assembly 12 and/or for the cooling system 14, based on the information contained in the window temperature signal. The processor 74 outputs one or more digital control signals to a digital-to-analog conversion system 76 which in turn provides one or more analog control signals to current drivers 78. In response to the control signal(s), the current drivers 78 regulate the power supplied to the heater layer 34 and/or to the cooling system 14. In one embodiment, the processor 74 provides a control signal through a digital I/O device 77 to a pulse-width modulator (PWM) control 80, which provides a signal that controls the operation of the current drivers 78. Alternatively, a low-pass filter (not shown) at the output of the PWM provides for continuous operation of the current drivers 78.

In another embodiment, temperature sensors may be located at the cooling system 14 and appropriately connected to the A/D system(s) and processor to provide closed-loop control of the cooling system as well.

In yet another embodiment, a detector cooling system 82 is located in thermally conductive relation to one or more of the detectors 28. The detector cooling system 82 may comprise any of the devices disclosed above as comprising the cooling system 14, and preferably comprises a Peltier-type thermoelectric device. The temperature control subsystem may also include temperature sensors, such as RTDs and/or thermistors, located in or adjacent to the detector cooling system 82, and electrical connections between these sensors and the asynchronous A/D system 72. The temperature sensors of the detector cooling system 82 provide detector temperature signals to the processor 74. In one embodiment, the detector cooling system 82 operates independently of the window temperature control system, and the detector cooling system temperature signals are sampled using the asynchronous A/D system 72. In accordance with the temperature control algorithm, the processor 74 determines appropriate control inputs for the detector cooling system 82, based on the information contained in the detector temperature signal. The processor 74 outputs digital control signals to the D/A system 76 which in turn provides analog control signals to the current drivers 78. In response to the control signals, the current drivers 78 regulate the power supplied to the detector cooling system 14. In one embodiment, the processor 74 also provides a control signal through the digital I/O device 77 and the PWM control 80, to control the operation of the detector cooling system 82 by the current drivers 78. Alternatively, a low-pass filter (not shown) at the output of the PWM provides for continuous operation of the current drivers 78.

In the data acquisition subsystem, the detectors 28 respond to the infrared energy E incident thereon by passing one or more analog detector signals to a preamp 84. The preamp 84 amplifies the detector signals and passes them to the synchronous A/D system 70, which converts the detector signals to digital form and passes them to the processor 74. The processor 74 determines the concentrations of the analyte(s) of interest, based on the detector signals and a concentration-analysis algorithm and/or phase/concentration regression model stored in a memory module 88. The concentration-analysis algorithm and/or phase/concentration regression model may be developed according to any of the analysis methodologies discussed herein. The processor may communicate the concentration results and/or other information to a display controller 86, which operates a display (not shown), such as an LCD display, to present the information to the user.

A watchdog timer 94 may be employed to ensure that the processor 74 is operating correctly. If the watchdog timer 94 does not receive a signal from the processor 74 within a specified time, the watchdog timer 94 resets the processor 74. The control system may also include a JTAG interface 96 to enable testing of the noninvasive system 10.

In one embodiment, the synchronous A/D system 70 comprises a 20-bit, 14 channel system, and the asynchronous A/D system 72 comprises a 16-bit, 16 channel system.

The preamp may comprise a 12-channel preamp corresponding to an array of 12 detectors 28.

The control system may also include a serial port 90 or other conventional data port to permit connection to a personal computer 92. The personal computer can be employed to update the algorithm(s) and/or phase/concentration regression model(s) stored in the memory module 88, or to download a compilation of analyte-concentration data from the noninvasive system. A real-time clock or other timing device may be accessible by the processor 74 to make any time-dependent calculations which may be desirable to a user.

2. Analysis Methodology

The detector(s) 28 of the noninvasive system 10 are used to detect the infrared energy emitted by the material sample S in various desired wavelengths. At each measured wavelength, the material sample S emits infrared energy at an intensity which varies over time. The time-varying intensities arise largely in response to the use of the window assembly 12 (including its heater layer 34) and the cooling system 14 to induce a thermal gradient in the material sample S. As used herein, "thermal gradient" is a broad term and is used in its ordinary sense and refers, without limitation, to a difference in temperature and/or thermal energy between different locations, such as different depths, of a material sample, which can be induced by any suitable method of increasing or decreasing the temperature and/or thermal energy in one or more locations of the sample. As will be discussed in detail below, the concentration of an analyte of interest (such as glucose) in the material sample S can be determined with a device such as the noninvasive system 10, by comparing the time-varying intensity profiles of the various measured wavelengths.

Analysis methodologies are discussed herein within the context of detecting the concentration of glucose within a material sample, such as a tissue sample, which includes a large proportion of water. However, it will evident that these methodologies are not limited to this context and may be applied to the detection of a wide variety of analytes within a wide variety of sample types. It should also be understood that other suitable analysis methodologies and suitable variations of the disclosed methodologies may be employed in operating an analyte detection system, such as the noninvasive system 10.

Figure 8:
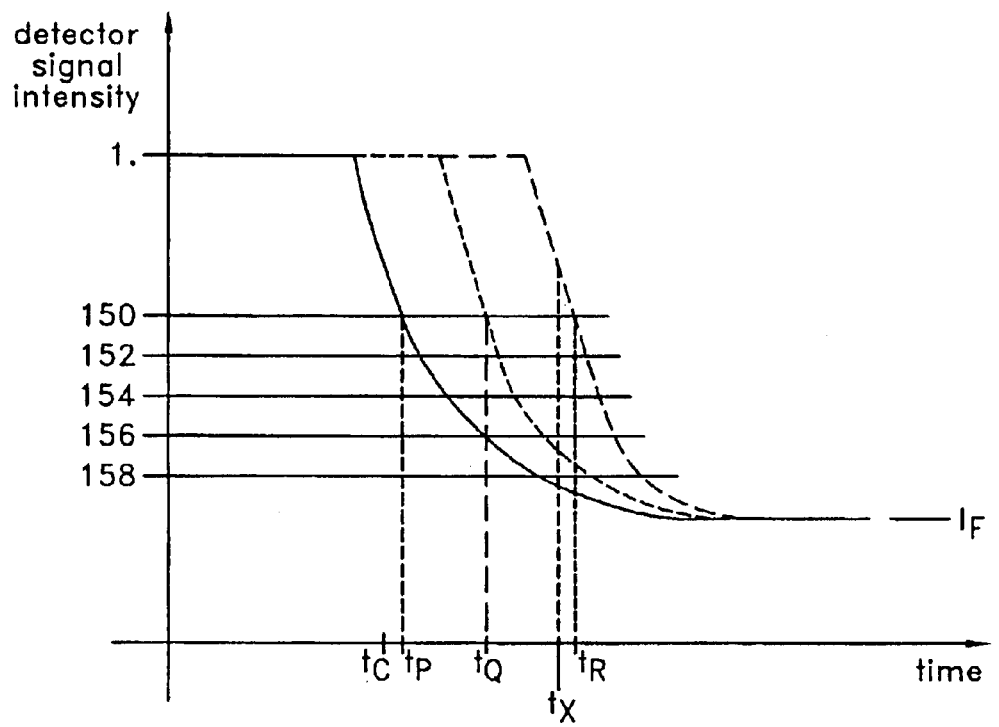
FIG. 8 depicts a first methodology for determining the concentration of an analyte of interest.

As shown in FIG. 8, a first reference signal P may be measured at a first reference wavelength. The first reference signal P is measured at a wavelength where water strongly absorbs (e.g., 2.9 μm or 6.1 μm). Because water strongly absorbs radiation at these wavelengths, the detector signal intensity is reduced at those wavelengths. Moreover, at these wavelengths water absorbs the photon emissions emanating from deep inside the sample. The net effect is that a signal emitted at these wavelengths from deep inside the sample is not easily detected. The first reference signal P is thus a good indicator of thermal-gradient effects near the sample surface and may be known as a surface reference signal. This signal may be calibrated and normalized, in the absence of heating or cooling applied to the sample, to a baseline value of 1. For greater accuracy, more than one first reference wavelength may be measured. For example, both 2.9 μm and 6.1 μm may be chosen as first reference wavelengths.

As further shown in FIG. 8, a second reference signal R may also be measured. The second signal R may be measured at a wavelength where water has very low absorbance (e.g., 3.6 μm or 4.2 μm). This second reference signal R thus provides the analyst with information concerning the deeper regions of the sample, whereas the first signal P provides information concerning the sample surface. This signal may also be calibrated and normalized, in the absence of heating or cooling applied to the sample, to a baseline value of 1. As with the first (surface) reference signal P, greater accuracy may be obtained by using more than one second (deep) reference signal R.

In order to determine analyte concentration, a third (analytical) signal Q is also measured. This signal is measured at an IR absorbance peak of the selected analyte. The IR absorbance peaks for glucose are in the range of about 6.5 μm to 1.0 μm. This detector signal may also be calibrated and normalized, in the absence of heating or cooling applied to the material sample S, to a baseline value of 1. As with the reference signals P, R, the analytical signal Q may be measured at more than one absorbance peak.

Optionally, or additionally, reference signals may be measured at wavelengths that bracket the analyte absorbance peak. These signals may be advantageously monitored at reference wavelengths which do not overlap the analyte absorbance peaks. Further, it is advantageous to measure reference wavelengths at absorbance peaks which do not overlap the absorbance peaks of other possible constituents contained in the sample.

a. Basic Thermal Gradient

As further shown in FIG. 8, the signal intensities P, Q, R are shown initially at the normalized baseline signal intensity of 1. This of course reflects the baseline radiative behavior of a test sample in the absence of applied heating or cooling. At a time $t_C$, the surface of the sample is subjected to a temperature event which induces a thermal gradient in the sample. The gradient can be induced by heating or cooling the sample surface. The example shown in FIG. 8 uses cooling, for example, using a 10° C. cooling event. In response to the cooling event, the intensities of the detector signals P, Q, R decrease over time.

Since the cooling of the sample is neither uniform nor instantaneous, the surface cools before the deeper regions of the sample cool. As each of the signals P, Q, R drop in intensity, a pattern emerges. Signal intensity declines as expected, but as the signals P, Q, R reach a given amplitude value (or series of amplitude values: 150, 152, 154, 156, 158), certain temporal effects are noted. After the cooling event is induced at $t_C$, the first (surface) reference signal P declines in amplitude most rapidly, reaching a checkpoint 150 first, at time $t_P$. This is due to the fact that the first reference signal P mirrors the sample's radiative characteristics near the surface of the sample. Since the sample surface cools before the underlying regions, the surface (first) reference signal P drops in intensity first.

Simultaneously, the second reference signal R is monitored. Since the second reference signal R corresponds to the radiation characteristics of deeper regions of the sample, which do not cool as rapidly as the surface (due to the time needed for the surface cooling to propagate into the deeper regions of the sample), the intensity of signal R does not decline until slightly later. Consequently, the signal R does not reach the magnitude 150 until some later time $t_R$. In other words, there exists a time delay between the time $t_P$ at which the amplitude of the first reference signal P reaches the checkpoint 150 and the time $t_R$ at which the second reference signal R reaches the same checkpoint 150. This time delay can be expressed as a phase difference $\Phi(\lambda)$. Additionally, a phase difference may be measured between the analytical signal Q and either or both reference signals P, R.

As the concentration of analyte increases, the amount of absorbance at the analytical wavelength increases. This reduces the intensity of the analytical signal Q in a concentration-dependent way. Consequently, the analytical signal Q reaches intensity 150 at some intermediate time $t_Q$. The higher the concentration of analyte, the more the analytical signal Q shifts to the left in FIG. 8. As a result, with increasing analyte concentration, the phase difference $\Phi(\lambda)$ decreases relative to the first (surface) reference signal P and increases relative to the second (deep tissue) reference signal R. The phase difference(s) $\Phi(\lambda)$ are directly related to analyte concentration and can be used to make accurate determinations of analyte concentration.

The phase difference $\Phi(\lambda)$ between the first (surface) reference signal P and the analytical signal Q is represented by the equation:

$$\Phi(\lambda)=|t_P-t_Q|$$

The magnitude of this phase difference decreases with increasing analyte concentration.

The phase difference $\Phi(\lambda)$ between the second (deep tissue) reference signal R and the analytical signal Q signal is represented by the equation:

$$\Phi(\lambda)=|t_Q-t_R|$$

The magnitude of this phase difference increases with increasing analyte concentration.

Accuracy may be enhanced by choosing several checkpoints, for example, 150, 152, 154, 156, and 158 and averaging the phase differences observed at each checkpoint. The accuracy of this method may be further enhanced by integrating the phase difference(s) continuously over the entire test period. Because in this example only a single temperature event (here, a cooling event) has been induced, the sample reaches a new lower equilibrium temperature and the signals stabilize at a new constant level $I_F$. Of course, the method works equally well with thermal gradients induced by heating or by the application or introduction of other forms of energy, such as but not limited to light, radiation, chemically induced heat, friction and vibration.

This methodology is not limited to the determination of phase difference. At any given time (for example, at a time $t_X$) the amplitude of the analytical signal Q may be compared to the amplitude of either or both of the reference signals P, R. The difference in amplitude may be observed and processed to determine analyte concentration.

This method, the variants disclosed herein, and the apparatus disclosed as suitable for application of the method(s), are not limited to the detection of in-vivo glucose concentration. The method and disclosed variants and apparatus may be used on human, animal, or even plant subjects, or on organic or inorganic compositions in a non-medical setting. The method may be used to take measurements of in-vivo or in-vitro samples of virtually any kind. The method is useful for measuring the concentration of a wide range of additional chemical analytes, including but not limited to, glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, hormones, as well as other chemical compounds. To detect a given analyte, one needs only to select appropriate analytical and reference wavelengths.

The method is adaptable and may be used to determine chemical concentrations in samples of body fluids (e.g., blood, urine or saliva) once they have been extracted from a patient. In fact, the method may be used for the measurement of in-vitro samples of virtually any kind.

b. Modulated Thermal Gradient

In some embodiments of the methodology described above, a periodically modulated thermal gradient can be employed to make accurate determinations of analyte concentration.

As previously shown in FIG. 8, once a thermal gradient is induced in the sample, the reference and analytical signals P, Q, R fall out of phase with respect to each other. This phase difference $\Phi(\lambda)$ is present whether the thermal gradient is induced through heating or cooling. By alternatively subjecting the test sample to cyclic pattern of heating, cooling, or alternately heating and cooling, an oscillating thermal gradient may be induced in a sample for an extended period of time.

Figure 9:
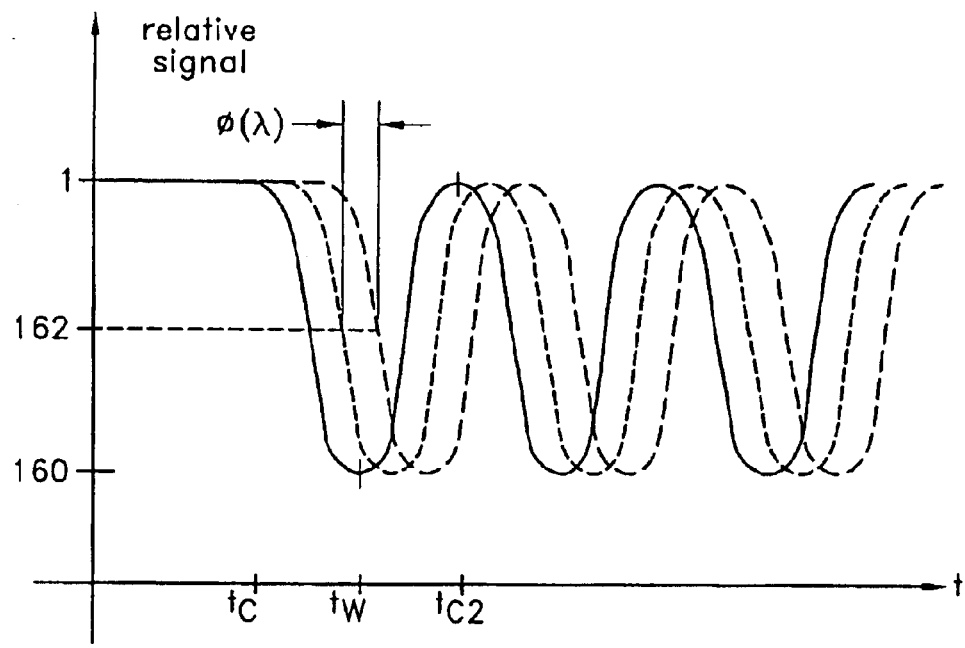
FIG. 9 depicts a second methodology for determining the concentration of an analyte of interest.

An oscillating thermal gradient is illustrated using a sinusoidally modulated gradient. FIG. 9 depicts detector signals emanating from a test sample. As with the methodology shown in FIG. 8, one or more reference signals J, L are measured. One or more analytical signals K are also monitored. These signals may be calibrated and normalized, in the absence of heating or cooling applied to the sample, to a baseline value of 1. FIG. 9 shows the signals after normalization. At some time $t_C$, a temperature event (e.g., cooling) is induced at the sample surface. This causes a decline in the detector signal. As shown in FIG. 8, the signals (P, Q, R) decline until the thermal gradient disappears and a new equilibrium detector signal $I_F$ is reached. In the method shown in FIG. 9, as the gradient begins to disappear at a signal intensity 160, a heating event, at a time $t_W$, is induced in the sample surface. As a result the detector output signals J, K, L will rise as the sample temperature rises. At some later time $t_{C2}$, another cooling event is induced, causing the temperature and detector signals to decline. This cycle of cooling and heating may be repeated over a time interval of arbitrary length. Moreover, if the cooling and heating events are timed properly, a periodically modulated thermal gradient may be induced in the test sample.

As previously explained in the discussions relating to FIG. 8, the phase difference $\Phi(\lambda)$ may be measured and used to determine analyte concentration. FIG. 9 shows that the first (surface) reference signal J declines and rises in intensity first. The second (deep tissue) reference signal L declines and rises in a time-delayed manner relative to the first reference signal J. The analytical signal K exhibits a time/phase delay dependent on the analyte concentration. With increasing concentration, the analytical signal K shifts to the left in FIG. 9. As with FIG. 8, the phase difference $\Phi(\lambda)$ may be measured. For example, a phase difference $\Phi(\lambda)$ between the second reference signal L and the analytical signal K, may be measured at a set amplitude 162 as shown in FIG. 9. Again, the magnitude of the phase signal reflects the analyte concentration of the sample.

The phase-difference information compiled by any of the methodologies disclosed herein can correlated by the control system 30 (see FIG. 1) with previously determined phase-difference information to determine the analyte concentration in the sample. This correlation could involve comparison of the phase-difference information received from analysis of the sample, with a data set containing the phase-difference profiles observed from analysis of wide variety of standards of known analyte concentration. In one embodiment, a phase/concentration curve or regression model is established by applying regression techniques to a set of phase-difference data observed in standards of known analyte concentration. This curve is used to estimate the analyte concentration in a sample based on the phase-difference information received from the sample.

Advantageously, the phase difference Φ(λ) may be measured continuously throughout the test period. The phase-difference measurements may be integrated over the entire test period for an extremely accurate measure of phase difference Φ(λ). Accuracy may also be improved by using more than one reference signal and/or more than one analytical signal.

As an alternative or as a supplement to measuring phase difference(s), differences in amplitude between the analytical and reference signal(s) may be measured and employed to determine analyte concentration. Additional details relating to this technique and not necessary to repeat here may be found in the Assignee's U.S. patent application Ser. No. 09/538,164, incorporated by reference below.

Additionally, these methods may be advantageously employed to simultaneously measure the concentration of one or more analytes. By choosing reference and analyte wavelengths that do not overlap, phase differences can be simultaneously measured and processed to determine analyte concentrations. Although FIG. 9 illustrates the method used in conjunction with a sinusoidally modulated thermal gradient, the principle applies to thermal gradients conforming to any periodic function. In more complex cases, analysis using signal processing with Fourier transforms or other techniques allows accurate determinations of phase difference Φ(λ) and analyte concentration.

Figure 10:
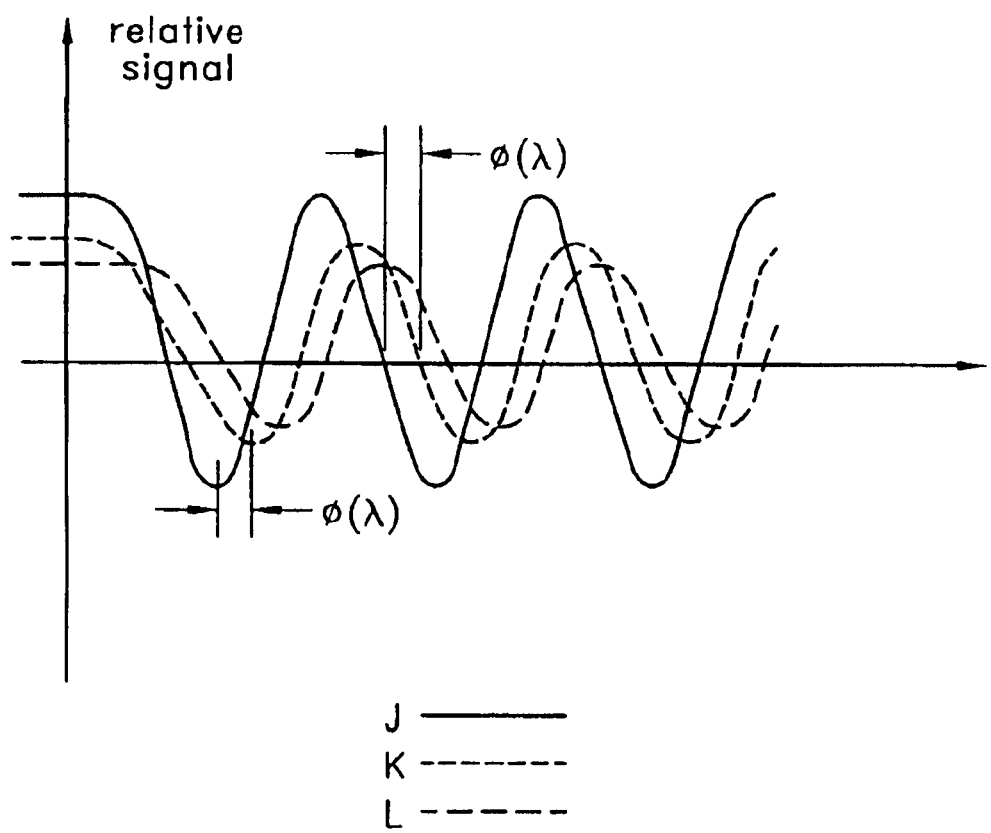
FIG. 10 depicts a third methodology for determining the concentration of an analyte of interest.

As shown in FIG. 10, the magnitude of the phase differences may be determined by measuring the time intervals between the amplitude peaks (or troughs) of the reference signals J, L and the analytical signal K. Alternatively, the time intervals between the "zero crossings" (the point at which the signal amplitude changes from positive to negative, or negative to positive) may be used to determine the phase difference between the analytical signal K and the reference signals J, L. This information is subsequently processed and a determination of analyte concentration may then be made. This particular method has the advantage of not requiring normalized signals.

As a further alternative, two or more driving frequencies may be employed to determine analyte concentrations at selected depths within the sample. A slow (e.g., 1 Hz) driving frequency creates a thermal gradient which penetrates deeper into the sample than the gradient created by a fast (e.g., 3 Hz) driving frequency. This is because the individual heating and/or cooling events are longer in duration where the driving frequency is lower. Thus, the use of a slow driving frequency provides analyte-concentration information from a deeper "slice" of the sample than does the use of a fast driving frequency.

It has been found that when analyzing a sample of human skin, a temperature event of 10° C. creates a thermal gradient which penetrates to a depth of about 150 $\mu$m, after about 500 ms of exposure. Consequently, a cooling/heating cycle or driving frequency of 1 Hz provides information to a depth of about 150 $\mu$m. It has also been determined that exposure to a temperature event of 10° C. for about 167 ms creates a thermal gradient that penetrates to a depth of about 50 $\mu$m. Therefore, a cooling/heating cycle of 3 Hz provides information to a depth of about 50 $\mu$m. By subtracting the detector signal information measured at a 3 Hz driving frequency from the detector signal information measured at a 1 Hz driving frequency, one can determine the analyte concentration(s) in the region of skin between 50 and 150 $\mu$m. Of course, a similar approach can be used to determine analyte concentrations at any desired depth range within any suitable type of sample.

Figure 11:
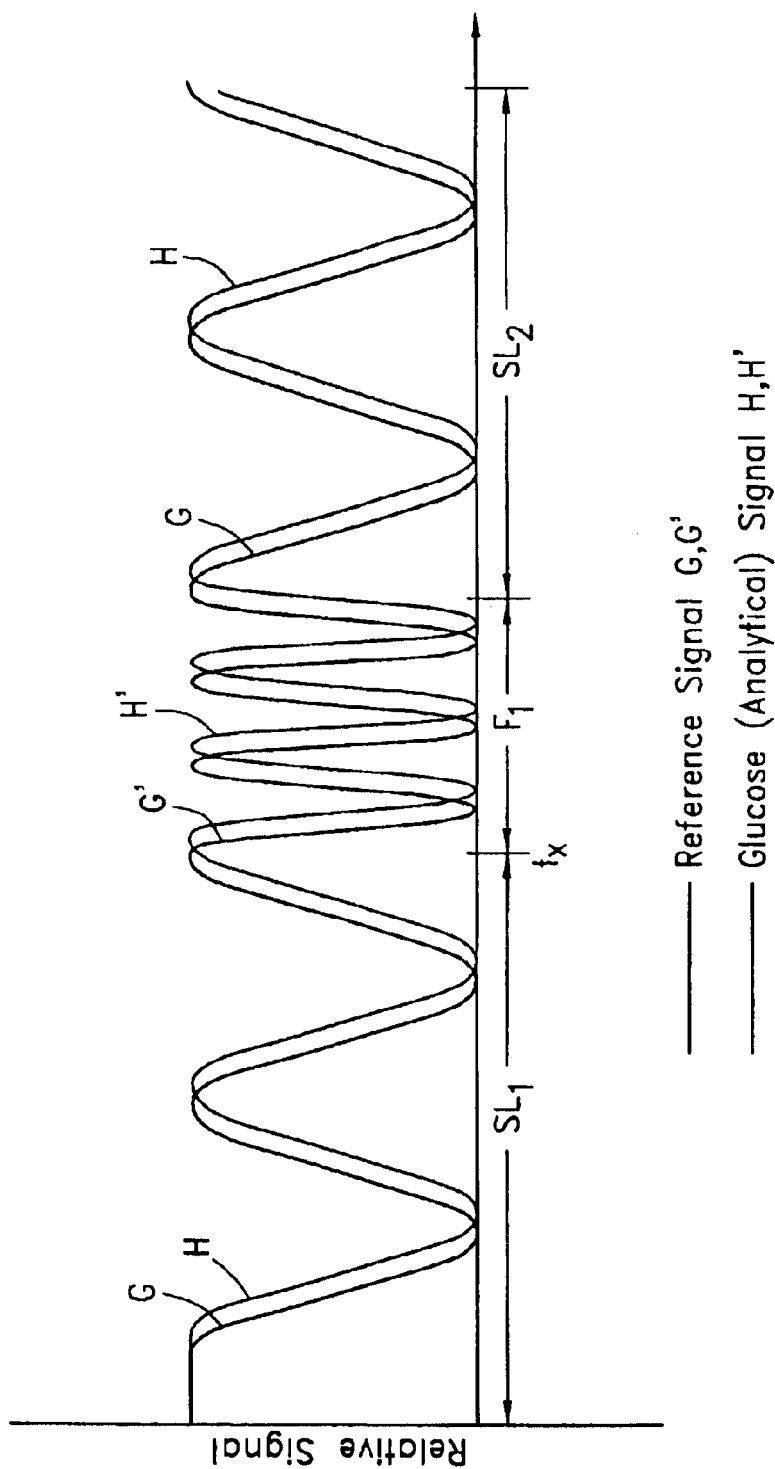
FIG. 11 depicts a fourth methodology for determining the concentration of an analyte of interest.

As shown in FIG. 11, alternating deep and shallow thermal gradients may be induced by alternating slow and fast driving frequencies. As with the methods described above, this variation also involves the detection and measurement of phase differences Φ(λ) between reference signals G, G' and analytical signals H, H'. Phase differences are measured at both fast (e.g., 3 Hz) and slow (e.g., 1 Hz) driving frequencies. The slow driving frequency may continue for an arbitrarily chosen number of cycles (in region $SL_1$), for example, two full cycles. Then the fast driving frequency is employed for a selected duration, in region $F_1$. The phase difference data is compiled in the same manner as disclosed above. In addition, the fast frequency (shallow sample) phase difference data may be subtracted from the slow frequency (deep sample) data to provide an accurate determination of analyte concentration in the region of the sample between the gradient penetration depth associated with the fast driving frequency and that associated with the slow driving frequency.

Figure 12:
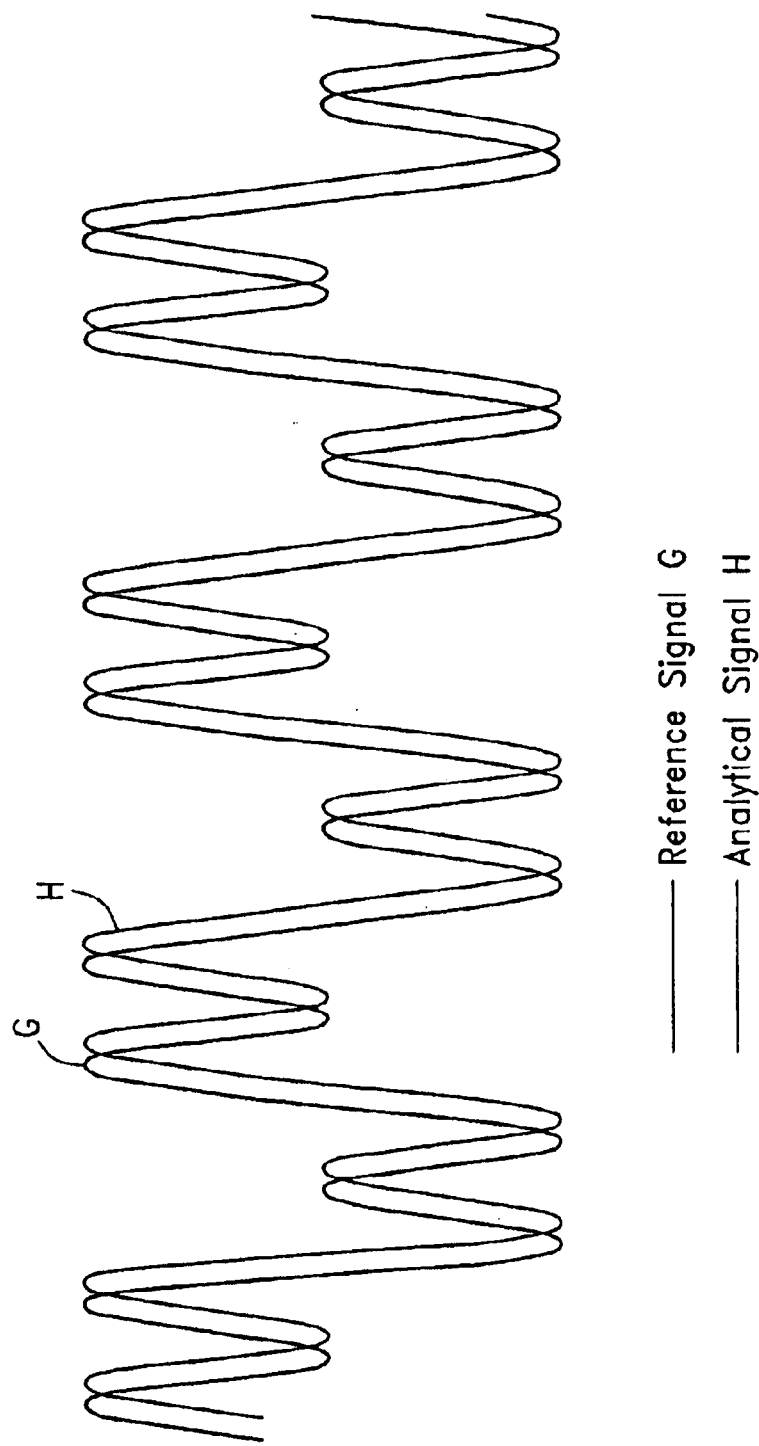
FIG. 12 depicts a fifth methodology for determining the concentration of an analyte of interest.

The driving frequencies (e.g., 1 Hz and 3 Hz) can be multiplexed as shown in FIG. 12. The fast (3 Hz) and slow (1 Hz) driving frequencies can be superimposed rather than sequentially implemented. During analysis, the data can be separated by frequency (using Fourier transform or other techniques) and independent measurements of phase delay at each of the driving frequencies may be calculated. Once resolved, the two sets of phase delay data are processed to determine absorbance and analyte concentration.

Additional details not necessary to repeat here may be found in U.S. Pat. No. 6,198,949, titled SOLID-STATE NON-INVASIVE INFRARED ABSORPTION SPECTROMETER FOR THE GENERATION AND CAPTURE OF THERMAL GRADIENT SPECTRA FROM LIVING TISSUE, issued Mar. 6, 2001; U.S. Pat. No. 6,161,028, titled METHOD FOR DETERMINING ANALYTE CONCENTRATION USING PERIODIC TEMPERATURE MODULATION AND PHASE DETECTION, issued Dec. 12, 2000; U.S. Pat. No. 5,877,500, titled MULTICHANNEL INFRARED DETECTOR WITH OPTICAL CONCENTRATORS FOR EACH CHANNEL, issued on Mar. 2, 1999; U.S. patent application Ser. No. 09/538,164, filed Mar. 30, 2000 and titled METHOD AND APPARATUS FOR DETERMINING ANALYTE CONCENTRATION USING PHASE AND MAGNITUDE DETECTION OF A RADIATION TRANSFER FUNCTION; U.S. Provisional Patent Application No. 60/336,404, filed Oct. 29, 2001, titled WINDOW ASSEMBLY; U.S. Provisional Patent Application No. 60/340,435, filed Dec. 12, 2001, titled CONTROL SYSTEM FOR BLOOD CONSTITUENT MONITOR; U.S. Provisional Patent Application No. 60/340,654, filed Dec. 12, 2001, titled SYSTEM AND METHOD FOR CONDUCTING AND DETECTING INFRARED RADIATION; U.S. Provisional Patent Application No. 60/336,294, filed Oct. 29, 2001, titled METHOD AND DEVICE FOR INCREASING ACCURACY OF BLOOD CONSTITUENT MEASUREMENT; and U.S. Provisional Patent Application No. 60/339,116, filed Nov. 7, 2001, titled METHOD AND APPARATUS FOR IMPROVING CLINICALLY SIGNIFICANT ACCURACY OF ANALYTE MEASUREMENTS. All of the above-mentioned patents, patent applications and publications are hereby incorporated by reference herein and made a part of this specification.

B. Whole-Blood Detection System

FIG. 13 is a schematic view of a reagentless whole-blood analyte detection system 200 (hereinafter "whole-blood system") in a preferred configuration. The whole-blood system 200 may comprise a radiation source 220, a filter 230, a cuvette 240 that includes a sample cell 242, and a radiation detector 250. The whole-blood system 200 preferably also comprises a signal processor 260 and a display 270. Although a cuvette 240 is shown here, other sample elements, as described below, could also be used in the system 200. The whole-blood system 200 can also comprise a sample extractor 280, which can be used to access bodily fluid from an appendage, such as the finger 290, forearm, or any other suitable location.

As used herein, the terms "whole-blood analyte detection system" and "whole-blood system" are broad, synonymous terms and are used in their ordinary sense and refer, without limitation, to analyte detection devices which can determine the concentration of an analyte in a material sample by passing electromagnetic radiation into the sample and detecting the absorbance of the radiation by the sample. As used herein, the term "whole-blood" is a broad term and is used in its ordinary sense and refers, without limitation, to blood that has been withdrawn from a patient but that has not been otherwise processed, e.g., it has not been hemolysed, lyophilized, centrifuged, or separated in any other manner, after being removed from the patient. Whole-blood may contain amounts of other fluids, such as interstitial fluid or intracellular fluid, which may enter the sample during the withdrawal process or are naturally present in the blood. It should be understood, however, that the whole-blood system 200 disclosed herein is not limited to analysis of whole-blood, as the whole-blood system 10 may, be employed to analyze other substances, such as saliva, urine, sweat, interstitial fluid, intracellular fluid, hemolysed, lyophilized, or centrifuged blood or any other organic or inorganic materials.

The whole-blood system 200 may comprise a near-patient testing system. As used herein, "near-patient testing system" is a broad term and is used in its ordinary sense, and includes, without limitation, test systems that are configured to be used where the patient is rather than exclusively in a laboratory, e.g., systems that can be used at a patient's home, in a clinic, in a hospital, or even in a mobile environment. Users of near-patient testing systems can include patients, family members of patients, clinicians, nurses, or doctors. A "near-patient testing system" could also include a "point-of-care" system.

The whole-blood system 200 may in one embodiment be configured to be operated easily by the patient or user. As such, the system 200 is preferably a portable device. As used herein, "portable" is a broad term and is used in its ordinary sense and means, without limitation, that the system 200 can be easily transported by the patient and used where convenient. For example, the system 200 is advantageously small. In one preferred embodiment, the system 200 is small enough to fit into a purse or backpack. In another embodiment, the system 200 is small enough to fit into a pants pocket. In still another embodiment, the system 200 is small enough to be held in the palm of a hand of the user.

Some of the embodiments described herein employ a sample element to hold a material sample, such as a sample of biological fluid. As used herein, "sample element" is a broad term and is used in its ordinary sense and includes, without limitation, structures that have a sample cell and at least one sample cell wall, but more generally includes any of a number of structures that can hold, support or contain a material sample and that allow electromagnetic radiation to pass through a sample held, supported or contained thereby; e.g., a cuvette, test strip, etc. As used herein, the term "disposable" when applied to a component, such as a sample element, is a broad term and is used in its ordinary sense and means, without limitation, that the component in question is used a finite number of times and then discarded. Some disposable components are used only once and then discarded. Other disposable components are used more than once and then discarded.

The radiation source 220 of the whole-blood system 200 emits electromagnetic radiation in any of a number of spectral ranges, e.g., within infrared wavelengths; in the mid-infrared wavelengths; above about 0.8 $\mu$m; between about 5.0 $\mu$m and about 20.0 $\mu$m; and/or between about 5.25 $\mu$m and about 12.0 $\mu$m. However, in other embodiments the whole-blood system 200 may employ a radiation source 220 which emits in wavelengths found anywhere from the visible spectrum through the microwave spectrum, for example anywhere from about 0.4 $\mu$m to greater than about 100 $\mu$m. In still further embodiments the radiation source emits electromagnetic radiation in wavelengths between about 3.5 $\mu$m and about 14 $\mu$m, or between about 0.8 $\mu$m and about 2.5 $\mu$m, or between about 2.5 $\mu$m and about 20 $\mu$m, or between about 20 $\mu$m and about 100 $\mu$m, or between about 6.85 $\mu$m and about 10.10 $\mu$m.

The radiation emitted from the source 220 is in one embodiment modulated at a frequency between about one-half hertz and about one hundred hertz, in another embodiment between about 2.5 hertz and about 7.5 hertz, in still another embodiment at about 50 hertz, and in yet another embodiment at about 5 hertz. With a modulated radiation source, ambient light sources, such as a flickering fluorescent lamp, can be more easily identified and rejected when analyzing the radiation incident on the detector 250. One source that is suitable for this application is produced by ION OPTICS, INC. and sold under the part number NL5LNC.

The filter 230 permits electromagnetic radiation of selected wavelengths to pass through and impinge upon the cuvette/sample element 240. Preferably, the filter 230 permits radiation at least at about the following wavelengths to pass through to the cuvette/sample element: 3.9, 4.0 $\mu$m, 4.05 $\mu$m, 4.2 $\mu$m, 4.75, 4.95 $\mu$m, 5.25 $\mu$m, 6.12 $\mu$m, 7.4 $\mu$m, 8.0 $\mu$m, 8.45 $\mu$m, 9.25 $\mu$m, 9.5 $\mu$m, 9.65 $\mu$m, 10.4 $\mu$m, 12.2 $\mu$m. In another embodiment, the filter 230 permits radiation at least at about the following wavelengths to pass through to the cuvette/sample element: 5.25 $\mu$m, 6.12 $\mu$m, 6.8 $\mu$m, 8.03 $\mu$m, 8.45 $\mu$m, 9.25 $\mu$m, 9.65 $\mu$m, 10.4 $\mu$m, 12 $\mu$m. In still another embodiment, the filter 230 permits radiation at least at about the following wavelengths to pass through to the cuvette/sample element: 6.85 $\mu$m, 6.97 $\mu$m, 7.39 $\mu$m, 8.23 $\mu$m, 8.62 $\mu$m, 9.02 $\mu$m, 9.22 $\mu$m, 9.43 $\mu$m, 9.62 $\mu$m, and 10.10 $\mu$m. The sets of wavelengths recited above correspond to specific embodiments within the scope of this disclosure. Furthermore, other subsets of the foregoing sets or other combinations of wavelengths can be selected. Finally, other sets of wavelengths can be selected within the scope of this disclosure based on cost of production, development time, availability, and other factors relating to cost, manufacturability, and time to market of the filters used to generate the selected wavelengths, and/or to reduce the total number of filters needed.

In one embodiment, the filter 230 is capable of cycling its passband among a variety of narrow spectral bands or a variety of selected wavelengths. The filter 230 may thus comprise a solid-state tunable infrared filter, such as that available from ION OPTICS INC. The filter 230 could also be implemented as a filter wheel with a plurality of fixed-passband filters mounted on the wheel, generally perpendicular to the direction of the radiation emitted by the source 220. Rotation of the filter wheel alternately presents filters that pass radiation at wavelengths that vary in accordance with the filters as they pass through the field of view of the detector 250.

The detector 250 preferably comprises a 3 mm long by 3 mm wide pyroelectric detector. Suitable examples are produced by DIAS Angewandte Sensorik GmbH of Dresden, Germany, or by BAE Systems (such as its TGS model detector). The detector 250 could alternatively comprise a thermopile, a bolometer, a silicon microbolometer, a lead-salt focal plane array, or a mercury-cadmium-telluride (MCT) detector. Whichever structure is used as the detector 250, it is desirably configured to respond to the radiation incident upon its active surface 254 to produce electrical signals that correspond to the incident radiation.

In one embodiment, the sample element comprises a cuvette 240 which in turn comprises a sample cell 242 configured to hold a sample of tissue and/or fluid (such as whole-blood, blood components, interstitial fluid, intercellular fluid, saliva, urine, sweat and/or other organic or inorganic materials) from a patient within its sample cell. The cuvette 240 is installed in the whole-blood system 200 with the sample cell 242 located at least partially in the optical path 243 between the radiation source 220 and the detector 250. Thus, when radiation is emitted from the source 220 through the filter 230 and the sample cell 242 of the cuvette 240, the detector 250 detects the radiation signal strength at the wavelength(s) of interest. Based on this signal strength, the signal processor 260 determines the degree to which the sample in the cell 242 absorbs radiation at the detected wavelength(s). The concentration of the analyte of interest is then determined from the absorption data via any suitable spectroscopic technique.

As shown in FIG. 13, the whole-blood system 200 can also comprise a sample extractor 280. As used herein, the term "sample extractor" is a broad term and is used in its ordinary sense and refers, without limitation, to any device which is suitable for drawing a sample material, such as whole-blood, other bodily fluids, or any other sample material, through the skin of a patient. In various embodiments, the sample extractor may comprise a lance, laser lance, iontophoretic sampler, gas-jet, fluid-jet or particle-jet perforator, ultrasonic enhancer (used with or without a chemical enhancer), or any other suitable device.

As shown in FIG. 13, the sample extractor 280 could form an opening in an appendage, such as the finger 290, to make whole-blood available to the cuvette 240. It should be understood that other appendages could be used to draw the sample, including but not limited to the forearm. With some embodiments of the sample extractor 280, the user forms a tiny hole or slice through the skin, through which flows a sample of bodily fluid such as whole-blood. Where the sample extractor 280 comprises a lance (see FIG. 14), the sample extractor 280 may comprise a sharp cutting implement made of metal or other rigid materials. One suitable laser lance is the Lasette Plus® produced by Cell Robotics International, Inc. of Albuquerque, N. Mex. If a laser lance, iontophoretic sampler, gas-jet or fluid-jet perforator is used as the sample extractor 280, it could be incorporated into the whole-blood system 200 (see FIG. 13), or it could be a separate device.

Additional information on laser lances can be found in U.S. Pat. No. 5,908,416, issued Jun. 1, 1999, titled LASER DERMAL PERFORATOR, the entirety of which is hereby incorporated by reference herein and made a part of this specification. One suitable gas-jet, fluid-jet or particle-jet perforator is disclosed in U.S. Pat. No. 6,207,400, issued Mar. 27, 2001, titled NON- OR MINIMALLY INVASIVE MONITORING METHODS USING PARTICLE DELIVERY METHODS, the entirety of which is hereby incorporated by reference herein and made a part of this specification. One suitable iontophoretic sampler is disclosed in U.S. Pat. No. 6,298,254, issued Oct. 2, 2001, titled DEVICE FOR SAMPLING SUBSTANCES USING ALTERNATING POLARITY OF IONTOPHORETIC CURRENT, the entirety of which is hereby incorporated by reference herein and made a part of this specification. One suitable ultrasonic enhancer, and chemical enhancers suitable for use therewith, are disclosed in U.S. Pat. No. 5,458,140, titled ENHANCEMENT OF TRANSDERMAL MONITORING APPLICATIONS WITH ULTRASOUND AND CHEMICAL ENHANCERS, issued Oct. 17, 1995, the entire disclosure of which is hereby incorporated by reference and made a part of this specification.

FIG. 14 shows one embodiment of a sample element, in the form of a cuvette 240, in greater detail. The cuvette 240 further comprises a sample supply passage 248, a pierceable portion 249, a first window 244, and a second window 246, with the sample cell 242 extending between the windows 244, 246. In one embodiment, the cuvette 240 does not have a second window 246. The first window 244 (or second window 246) is one form of a sample cell wall; in other embodiments of the sample elements and cuvettes disclosed herein, any sample cell wall may be used that at least partially contains, holds or supports a material sample, such as a biological fluid sample, and which is transmissive of at least some bands of electromagnetic radiation, and which may but need not be transmissive of electromagnetic radiation in the visible range. The pierceable portion 249 is an area of the sample supply passage 248 that can be pierced by suitable embodiments of the sample extractor 280. Suitable embodiments of the sample extractor 280 can pierce the portion 249 and the appendage 290 to create a wound in the appendage 290 and to provide an inlet for the blood or other fluid from the wound to enter the cuvette 240. (The sample extractor 280 is shown on the opposite side of the sample element in FIG. 14, as compared to FIG. 13, as it may pierce the portion 249 from either side.)

The windows 244, 246 are preferably optically transmissive in the range of electromagnetic radiation that is emitted by the source 220, or that is permitted to pass through the filter 230. In one embodiment, the material that makes up the windows 244, 246 is completely transmissive, i.e., it does not absorb any of the electromagnetic radiation from the source 220 and filter 230 that is incident upon it. In another embodiment, the material of the windows 244, 246 has some absorption in the electromagnetic range of interest, but its absorption is negligible. In yet another embodiment, the absorption of the material of the windows 244, 246 is not negligible, but it is known and stable for a relatively long period of time. In another embodiment, the absorption of the windows 244, 246 is stable for only a relatively short period of time, but the whole-blood system 200 is configured to observe the absorption of the material and eliminate it from the analyte measurement before the material properties can change measurably.

The windows 244, 246 are made of polypropylene in one embodiment. In another embodiment, the windows 244, 246 are made of polyethylene. Polyethylene and polypropylene are materials having particularly advantageous properties for handling and manufacturing, as is known in the art. Also, polypropylene can be arranged in a number of structures, e.g., isotactic, atactic and syndiotactic, which may enhance the flow characteristics of the sample in the sample element.

Preferably the windows 244, 246 are made of durable and easily manufactureable materials, such as the above-mentioned polypropylene or polyethylene, or silicon or any other suitable material. The windows 244, 246 can be made of any suitable polymer, which can be isotactic, atactic or syndiotactic in structure.

The distance between the windows 244, 246 comprises an optical pathlength and can be between about 1 $\mu$m and about 100 $\mu$m. In one embodiment, the optical pathlength is between about 10 $\mu$m and about 40 $\mu$m, or between about 25 $\mu$m and about 60 $\mu$m, or between about 30 $\mu$m and about 50 $\mu$m. In still another embodiment, the optical pathlength is about 25 $\mu$m. The transverse size of each of the windows 244, 246 is preferably about equal to the size of the detector 250. In one embodiment, the windows are round with a diameter of about 3 mm. In this embodiment, where the optical pathlength is about 25 $\mu$m the volume of the sample cell 242 is about 0.177 $\mu$L. In one embodiment, the length of the sample supply passage 248 is about 6 mm, the height of the sample supply passage 248 is about 1 mm, and the thickness of the sample supply passage 248 is about equal to the thickness of the sample cell, e.g., 25 $\mu$m. The volume of the sample supply passage is about 0.150 $\mu$L. Thus, the total volume of the cuvette 240 in one embodiment is about 0.327 $\mu$L. Of course, the volume of the cuvette 240/sample cell 242/etc. can vary, depending on many variables, such as the size and sensitivity of the detectors 250, the intensity of the radiation emitted by the source 220, the expected flow properties of the sample, and whether flow enhancers (discussed below) are incorporated into the cuvette 240. The transport of fluid to the sample cell 242 is achieved preferably through capillary action, but may also be achieved through wicking, or a combination of wicking and capillary action.

Figure 16A:
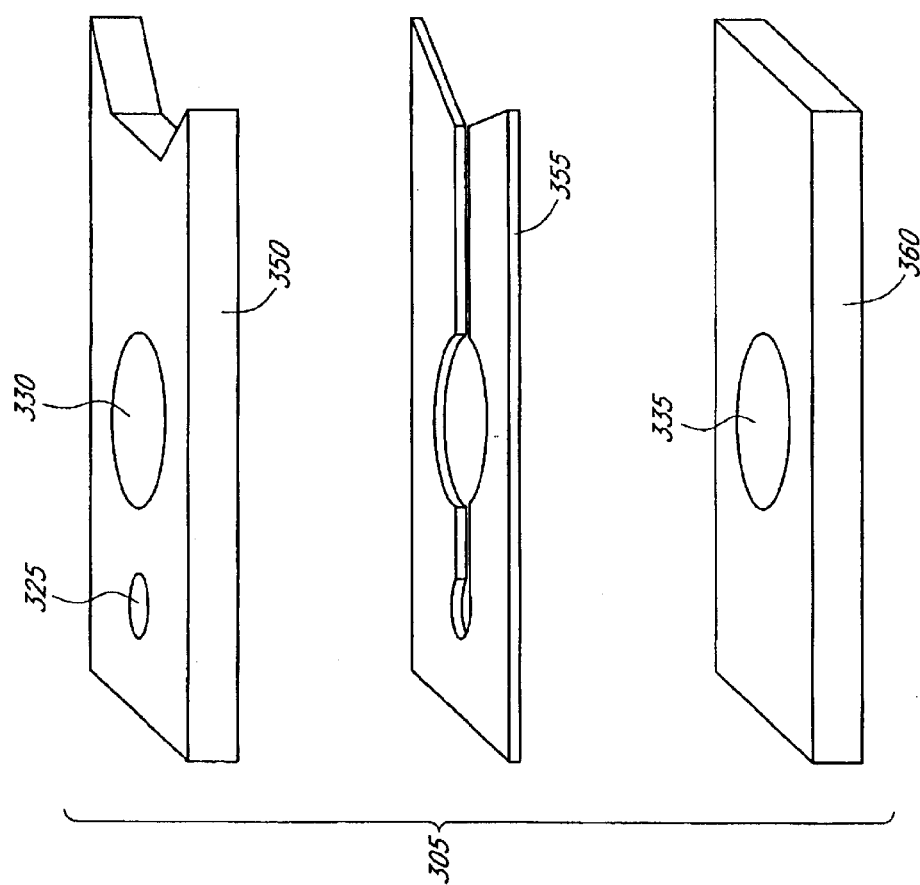
FIG. 16A is an exploded perspective view of the cuvette of FIG. 15.

FIGS. 15–17 depict another embodiment of a cuvette 305 that could be used in connection with the whole-blood system 200. The cuvette 305 comprises a sample cell 310, a sample supply passage 315, an air vent passage 320, and a vent 325. As best seen in FIGS. 16, 16A and 17, the cuvette also comprises a first sample cell window 330 having an inner side 332, and a second sample cell window 335 having an inner side 337. As discussed above, the window(s) 330/335 in some embodiments also comprise sample cell wall(s). The cuvette 305 also comprises an opening 317 at the end of the sample supply passage 315 opposite the sample cell 310. The cuvette 305 is preferably about ¼–⅛ inch wide and about ¾ inch long; however, other dimensions are possible while still achieving the advantages of the cuvette 305.

The sample cell 310 is defined between the inner side 332 of the first sample cell window 330 and the inner side 337 of the second sample cell window 335. The perpendicular distance T between the two inner sides 332, 337 comprises an optical pathlength that can be between about 1 $\mu$m and about 1.22 mm. The optical pathlength can alternatively be between about 1 $\mu$m and about 100 $\mu$m. The optical pathlength could still alternatively be about 80 $\mu$m, but is preferably between about 10 $\mu$m and about 50 $\mu$m. In another embodiment, the optical pathlength is about 25 $\mu$m. The windows 330, 335 are preferably formed from any of the materials discussed above as possessing sufficient radiation transmissivity. The thickness of each window is preferably as small as possible without overly weakening the sample cell 310 or cuvette 305.

Once a wound is made in the appendage 290, the opening 317 of the sample supply passage 315 of the cuvette 305 is placed in contact with the fluid that flows from the wound.

In another embodiment, the sample is obtained without creating a wound, e.g. as is done with a saliva sample. In that case, the opening 317 of the sample supply passage 315 of the cuvette 305 is placed in contact with the fluid obtained without creating a wound. The fluid is then transported through the sample supply passage 315 and into the sample cell 310 via capillary action. The air vent passage 320 improves the capillary action by preventing the buildup of air pressure within the cuvette and allowing the blood to displace the air as the blood flows therein.

Other mechanisms may be employed to transport the sample to the sample cell 310. For example, wicking could be used by providing a wicking material in at least a portion of the sample supply passage 315. In another variation, wicking and capillary action could be used together to transport the sample to the sample cell 310. Membranes could also be positioned within the sample supply passage 315 to move the blood while at the same time filtering out components that might complicate the optical measurement performed by the whole-blood system 200.

FIGS. 16 and 16A depict one approach to constructing the cuvette 305. In this approach, the cuvette 305 comprises a first layer 350, a second layer 355, and a third layer 360. The second layer 355 is positioned between the first layer 350 and the third layer 360. The first layer 350 forms the first sample cell window 330 and the vent 325. As mentioned above, the vent 325 provides an escape for the air that is in the sample cell 310. While the vent 325 is shown on the first layer 350, it could also be positioned on the third layer 360, or could be a cutout in the second layer, and would then be located between the first layer 360 and the third layer 360 The third layer 360 forms the second sample cell window 335.

The second layer 355 may be formed entirely of an adhesive that joins the first and third layers 350, 360. In other embodiments, the second layer may be formed from similar materials as the first and third layers, or any other suitable material. The second layer 355 may also be formed as a carrier with an adhesive deposited on both sides thereof. The second layer 355 forms the sample supply passage 315, the air vent passage 320, and the sample cell 310. The thickness of the second layer 355 can be between about 1 $\mu$m and about 1.22 mm. This thickness can alternatively be between about 1 $\mu$m and about 100 $\mu$m. This thickness could alternatively be about 80 $\mu$m, but is preferably between about 10 $\mu$m and about 50 $\mu$m. In another embodiment, the second layer thickness is about 25 $\mu$m.

In other embodiments, the second layer 355 can be constructed as an adhesive film having a cutout portion to define the passages 315, 320, or as a cutout surrounded by adhesive.

Further information can be found in U.S. patent application Ser. No. 10/055,875, filed Jan. 21, 2002, titled REAGENT-LESS WHOLE-BLOOD GLUCOSE METER. The entirety of this patent application is hereby incorporated by reference herein and made a part of this specification.

II. Method for Adjusting a Blood Analyte Measurement

It has been found that phase measurements that correlate to analyte concentrations are affected by changes in the amounts of other substances in the sample that are also IR absorbers. For the glucose measurement embodiment, for example, when a non-invasive instrument 10 is placed against the sample (such as a forearm), the skin no longer breathes, and the water content of the sample increases. This increase in water concentration affects the phase measurements which are intended to relate to glucose concentration, even though the glucose concentration stays the same. Sample hydration levels can also vary between time separated measurements.

A number of ways may be utilized to help compensate for this effect. It may in some cases be possible to choose filters which pass wavelengths such that each pair or multiple channels se the same change in analytes during measurement (at constant glucose). In some cases, it may also be possible to determine and separate the specific contributions of the water and the glucose on the absorption and measured phase characteristics of the sample. This technique is described in additional detail in Assignee's U.S. patent application Ser. No. _____ [Attorney Docket No. OPTIS.043A], filed on Nov. 8, 2002, entitled METHOD FOR TRANSFORMING PHASE SPECTRA TO ABSORPTION SPECTRA, which claims priority to Provisional Application Nos. 60/337,406 and 60/340,773, the entirety of all of which are hereby incorporated by reference and made a part of this specification.

In other embodiments, a hydration correction process may be provided for calibration and correction of data acquired by the noninvasive system 10 from a sample S comprising a sought-after analyte concentration and a second, changing analyte value, such that the concentration of the sought-after analyte may be determined. Preferably, the noninvasive system 10 is used to measure at least two different wavelengths in order to distinguish between the sought-after analyte concentration value and the changing analyte value.

In one embodiment, the changing analyte is water. In this case, the sought-after analyte concentration can be determined by testing a sample having a known sought-after analyte concentration and a changing hydration concentration, and then using the resulting data to compute a hydration correction coefficient. Once computed, the hydration correction coefficient can be used for determining concentrations of the sought-after analyte in other samples having unknown hydration levels. Methods for determining values for the hydration correction coefficient and subsequent determination of analyte concentrations are discussed in detailed below.

A. Hydration Correction

Figure 18:
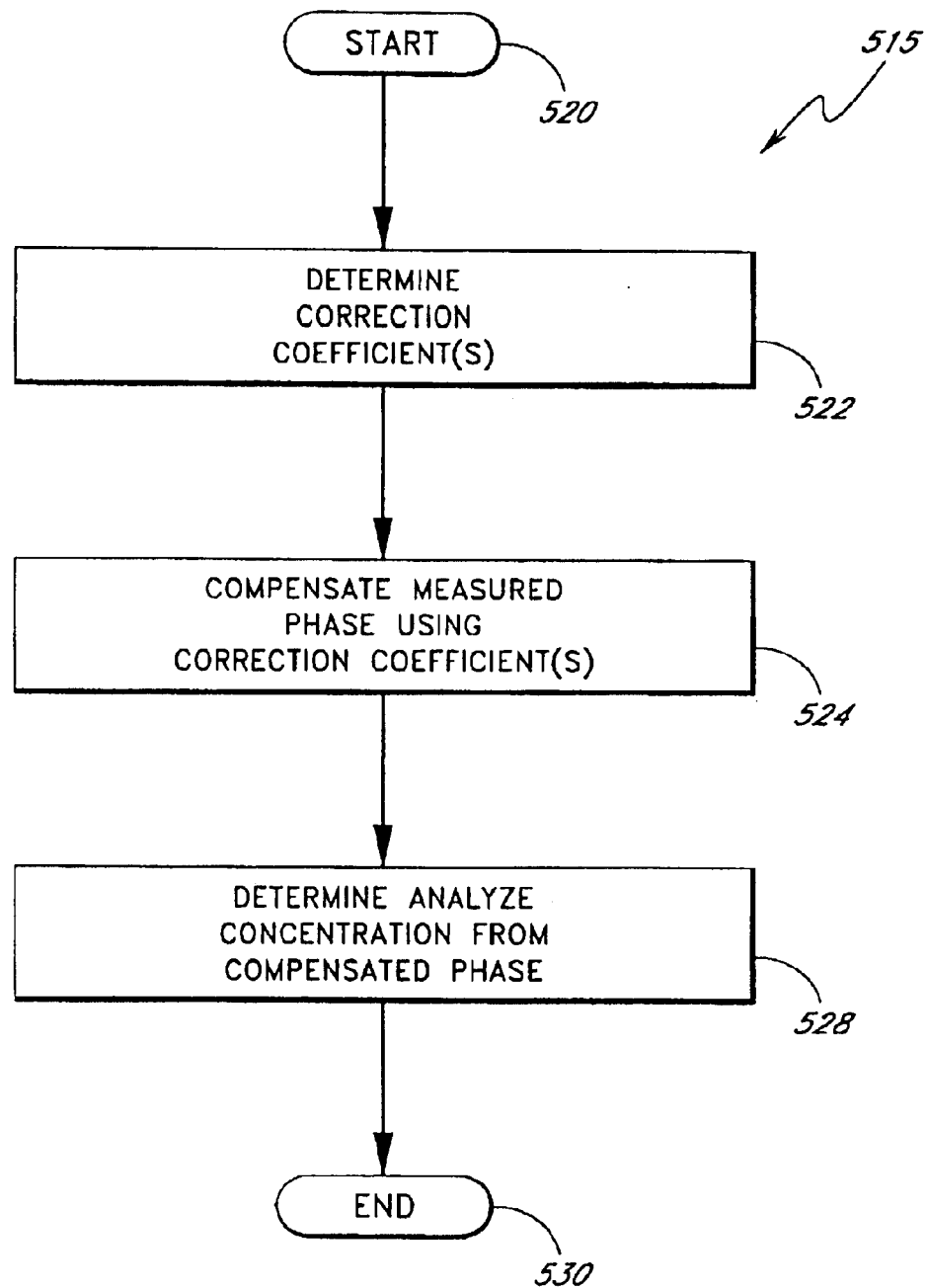
FIG. 18 is a high level flow chart illustrating a hydration correction process.

FIG. 18 is a flow chart illustrating one embodiment of a hydration correction process 515. It will be appreciated that in one embodiment, the sample S may comprise human tissue, to which heating and/or cooling is applied such that IR radiation is emitted therefrom and into the noninvasive system 10 (FIG. 1) wherein an optical signal is received by optical detectors. It will be further appreciated that in another embodiment, the sample S is analyzed in-vitro and IR radiation may be emitted from a source and transmitted directly through the sample S, such as with the whole-blood system 200.

As shown in FIG. 18, the hydration correction process 515 initiates at a start state 520 and proceeds to a state 522 wherein a hydration correction coefficient (referred to below as either $C_h$ or $f_h$) is calculated. In some embodiments, two or more correction coefficients are calculated. The system then compensates a measured phase value using the correction coefficient(s) at block 524. At block 528, the concentration of the analyte of interest is then determined using the compensated phase measurement. The system then moves to an end state 530.

As mentioned above, the noninvasive system 10 is advantageously used to measure at least two different wavelengths of electromagnetic radiation emitted by the sample S in order to distinguish between a sought-after analyte concentration value and a second, changing analyte value, and thereby to determine the sought-after analyte concentration. In a preferred embodiment, the sought-after analyte concentration can be determined by testing a sample having a known analyte concentration and a changing hydration concentration, and then using the resulting data to compute a hydration correction coefficient $C_h$. The hydration correction coefficient can then be used for determining concentrations of the sought-after analyte in other samples that have unknown hydration levels.

In one embodiment, the noninvasive system 10 is used to measure an analyte wavelength A, a reference wavelength R and a hydration wavelength H, yielding the phases $\Phi_A$, $\Phi_R$ and $\Phi_H$, respectively. As detailed above, the phase data is used to determine a value of the hydration correction coefficient. In one embodiment, the hydration correction coefficient $C_h$ may be expressed linearly in the form $$C_h = \frac{\Phi_A^C - \Phi_R^C}{\Phi_R^C - \Phi_H^C} = \frac{\Delta\Phi_{A-R}^C}{\Delta\Phi_{R-H}^C}, \qquad \text{Equation 1}$$

wherein the superscript C represents a known constant analyte concentration; $\Phi_A$, $\Phi_R$ and $\Phi_H$ are the phases observed at the wavelengths A, R and H, respectively; and Δ represents a change in phase. As will be appreciated by those of ordinary skill in the art, the above expression is one example of a linear equation. In another embodiment, the hydration correction coefficient may be expressed in nonlinear form by relating the numerator of the above expression to a function of the form $$\Delta\Phi_{A-R}^C = A_H(\Delta\Phi_{R-H}^C)^2 + B_H(\Delta\Phi_{R-H}^C),$$

wherein $A_H$ and $B_H$ are coefficients. The coefficients $A_H$ and $B_H$ may be determined by measuring $\Delta\Phi_{R-H}^C$ and $\Delta\Phi_{A-R}^C$ for at least two different analyte concentrations and then solving the resulting equations for $A_H$ and $B_H$. In still other embodiments, the hydration correction coefficient may be expressed by utilizing linear or nonlinear equations possessing more than two coefficients.

For the purpose of illustration, the main constituent in blood is water and the analyte of interest is glucose. For this case, a glucose wavelength may be measured at 9.5 μm, a reference wavelength may be measured at 8.4 μm and a hydration wavelength may be measured at 11.1 μm. In one embodiment, wherein the above-discussed linear form of the hydration correction coefficient is utilized, the hydration correction coefficient is given by $$C_h = \frac{\Phi_{9.5\mu m}^G - \Phi_{8.4\mu m}^G}{\Phi_{8.4\mu m}^G - \Phi_{11.1\mu m}^G} = \frac{\Delta\Phi_{9.5-8.4}^G}{\Delta\Phi_{8.4-11.1}^G},$$

where the superscript G represents a known constant glucose concentration. In another embodiment, wherein the above-discussed nonlinear form of the hydration correction coefficient is used, the numerator of the hydration correction coefficient is expressible as $$\Delta\Phi_{9.5-8.8}^G = A_H(\Delta\Phi_{8.4-11.1}^G)^2 + B_H(\Delta 101_{8.4-11.1}^G).$$

As mentioned above, any expression suitable for determination of the hydration correction coefficient can be utilized.

To determine a value for the hydration correction coefficient $C_h$, a plurality of continuous measurement runs (or "thumps") may be performed with human subjects or calibration standards or other samples having relatively constant known glucose concentrations. Depending on the particular expression used for $C_h$, a value for the hydration correction coefficient may be obtained either through direct linear determination or through determination of the coefficients $A_H$ and $B_H$, or through determination of more than two coefficients.

Once the value of the hydration correction coefficient $C_h$ is determined, as discussed above, measurements may be performed on subjects having unknown glucose concentrations. The phase corresponding to the measured glucose concentration can then be determined by using the expression $$\Phi^G = \Delta\Phi_{A-R} - C_h(\Delta\Phi_{R-H}), \quad \text{Equation 2}$$

wherein $\Phi_A$, $\Phi_R$ and $\Phi_H$ are the phases observed at the wavelengths A, R and H, respectively; and $\Delta$ represents a change in phase. For the purpose of illustration, in the above-discussed case wherein the glucose wavelength is measured at 9.5 μm, the reference wavelength is measured at 8.4 μm and the hydration wavelength may be measured at 11.1 μm, equation 2 takes the form $$\Phi^G = \Delta\Phi_{9.5-8.4} - C_h(\Delta\Phi_{8.4-11.1}).$$

Thus, each new subsequent measurement produces values for $\Delta\Phi_{9.5-8.4}$ and $\Delta\Phi_{8.4-11.1}$, and because the value of the hydration correction coefficient $C_h$ is known, the unknown glucose concentration can be determined. A specific example of this process may be described as follows wherein μm=micrometers, Δ=change, and ϕ=phase angle from IR detector As described above, three wavelengths may be used as benchmarks and references to separate glucose from hydration after taking measurements from a patient. These wavelengths may vary during different tests.

1. Glucose at 9.5 μm
2. Reference at 8.4 μm
3. Water at 11.1 μm

The equation used:

$$\Delta\phi_{9-8} = \Phi_{9.5\ \mu m} - \Phi_{8.4\ \mu m}, \quad \Delta\phi_{8-11} = \Phi_{8.4\ \mu m} - \Phi_{11.1\ \mu m}$$

First, one or several sets of phase measurements are taken from a sample (such as a forearm of a subject) when the sample has a known and substantially constant glucose (G) concentration. From this data, the following factor for hydration correction ($f_h$):

$$f_h = \frac{\Delta\phi_{9-8}^G}{\Delta\phi_{8-11}^G}$$

Each new subsequent measurement will produce $\Delta\phi_{9-8}$ and $\Delta\Phi_{8-11}$ at an unknown glucose level. Using the correction factor, $f_h$:

$$\Delta\phi_{9-8} = f_h \cdot \Delta\phi_{8-11}$$

the predicted (prime) value of $\Delta\Phi_{9-8}$ for a measure value of $\Delta\Phi_{8-11}$ is produced. Then the compensated phase difference corresponding to the measured glucose is given by $$\phi_G = \Delta\phi_{9-8} - \Delta\phi_{9-8}'$$

The glucose concentration is then found by applying the sensitivity and offset values to $\phi_G$.

Glucose (mg/dL)=($\phi_G$·sensitivity+offset)+(glucose value at calibration)

wherein the glucose value at calibration is the known constant value which was present during the testing per- formed to produce the initial $f_h$. When this technique is used, the raw measured phase difference values may be continually updated with correction factor. In this case, changes in the glucose level from the original constant value produce a change in the compensated phase value which is then correlated to the new glucose concentration. In contrast, the effect of changes in sample hydration level during the measurement or on a series of measurements is reduced.

Figure 19:
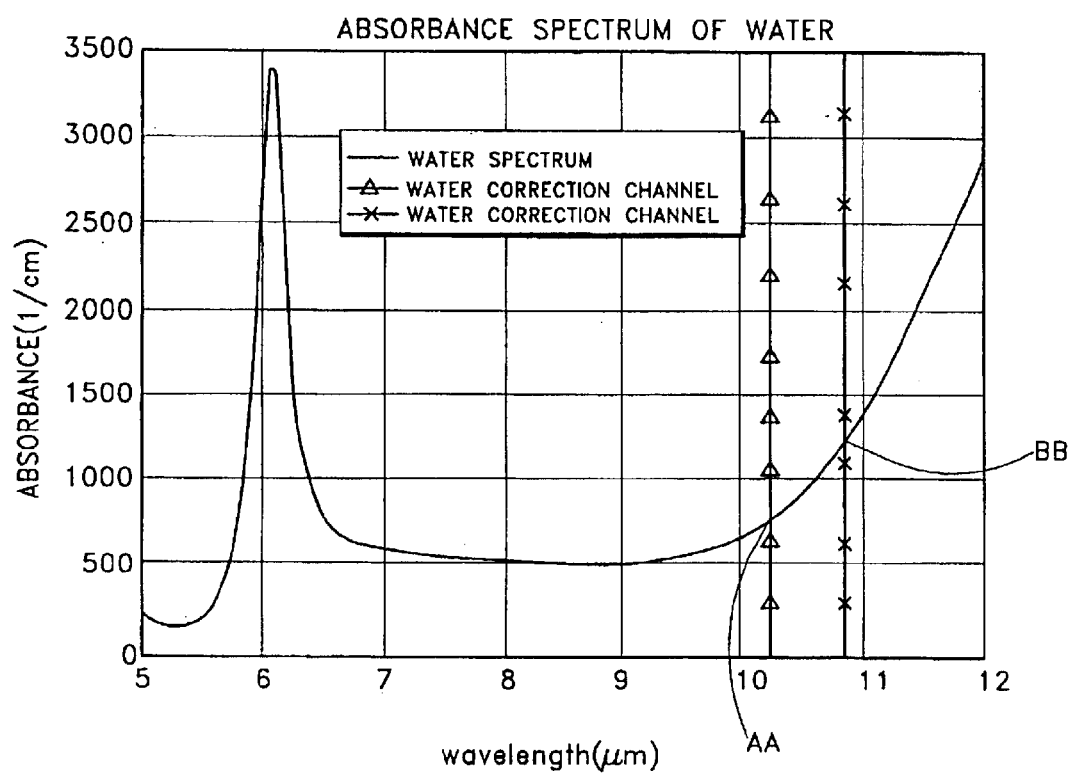
FIG. 19 is a graph illustrating a water absorbance spectrum, and shows two hydration correction wavelengths.

In another embodiment, a value of the hydration correction coefficient $f_h$ can be determined based on a difference in the absorbance of water at the wavelength 10.25 μm and the absorbance of water at the wavelength 10.855 μm. FIG. 19 is a graph illustrating the absorbance spectrum of water, and highlights the absorbance of water at the wavelengths 10.25 μm (at point AA) and 10.855 μm (at point BB). In this embodiment, the hydration coefficient is derived from the ratio of (1) the difference, in a measurement performed on the sample S, between the phase measured at a wavelength of about 10.25 μm and the phase measured at a wavelength of about 10.855 μm; to (2) the difference, in a measurement performed on a sample of water, between the phase measured at a wavelength of about 10.25 μm and the phase measured at a wavelength of about 10.855 μm. The hydration correction coefficient is thus expressed as $$f_h = \frac{\Phi_{10.855\mu m}^S - \Phi_{10.25\mu m}^S}{\Phi_{10.855\mu m}^H - \Phi_{10.25\mu m}^H}, \quad \text{Equation 3}$$

wherein $\Phi^S$ and $\Phi^H$ are the phases of the sample and water, respectively, and the subscripts denote the two wavelengths at which the phases are measured. In one embodiment, the value for the hydration correction coefficient is determined by performing a plurality of continuous measurement runs (or "thumps"). Once the hydration correction coefficient is determined, the phase spectrum of the sample S can be "hydration corrected" by using an expression of the form $$\Phi_{h,\lambda} = \Phi_\lambda^S - f_h(\Phi_\lambda^H), \quad \text{Equation 4}$$

wherein $\Phi_{h,\lambda}$ is the hydration-free phase spectrum of the sample, and the subscript λ indicates that the phase is expressible over a spectrum of wavelengths. Once values for $\Phi_{h,\lambda}$ are obtained, the analyte concentration within the sample S may be determined as discussed above.

FIGS. 20A through 24 are graphs illustrating the results of applying the hydration correction process to an exemplary use environment wherein the noninvasive system 10 is used to test a plurality of stable hydrogels having different, but known, hydration levels.

It will be appreciated that the hydrogels were formed to serve as human skin models having various degrees of hydration and glucose content. Each hydrogel was prepared by casting a slab of at least about 1-millimeter thickness from gelatin solutions that also contained gum Arabic as a stable surrogate for glucose, as well as latex particles and polymetric dyes to serve as markers for identification. Each hydrogel was allowed to solidify into a gel, after which the gelatin was cross-linked with glutaraldehyde to provide long-term mechanical and chemical stability of the human skin model. Various degrees of hydration were obtained by heat shrinking the material in hot water for different lengths of time followed by relation for several days. The final materials were kept in water with a bacterial growth inhibitor.

Figure 20A:
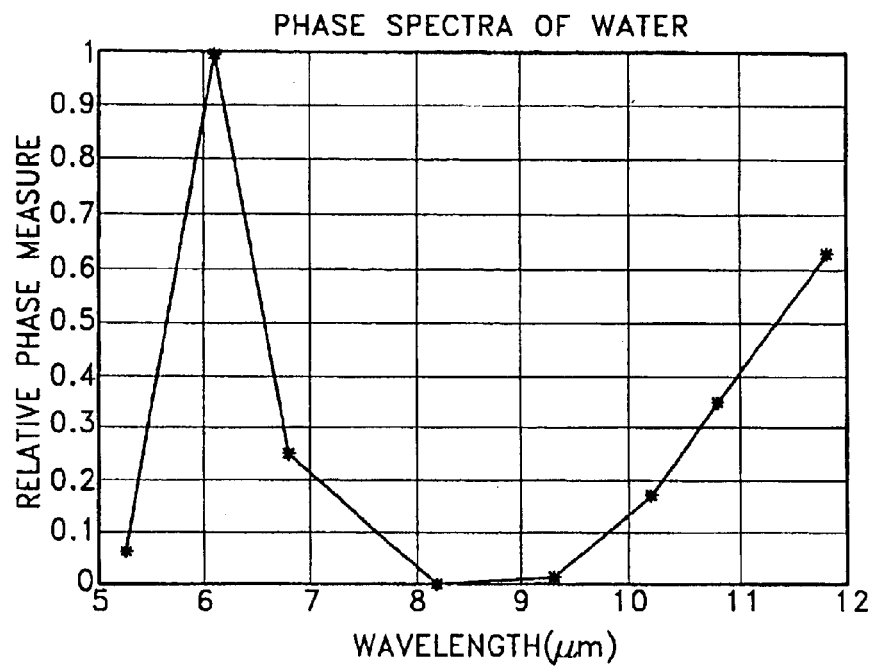
FIGS. 20A through 24 are graphs illustrating results of applying one embodiment of a hydration correction analysis to a plurality of hydrogels having different, but known, hydration levels.
Figure 20B:
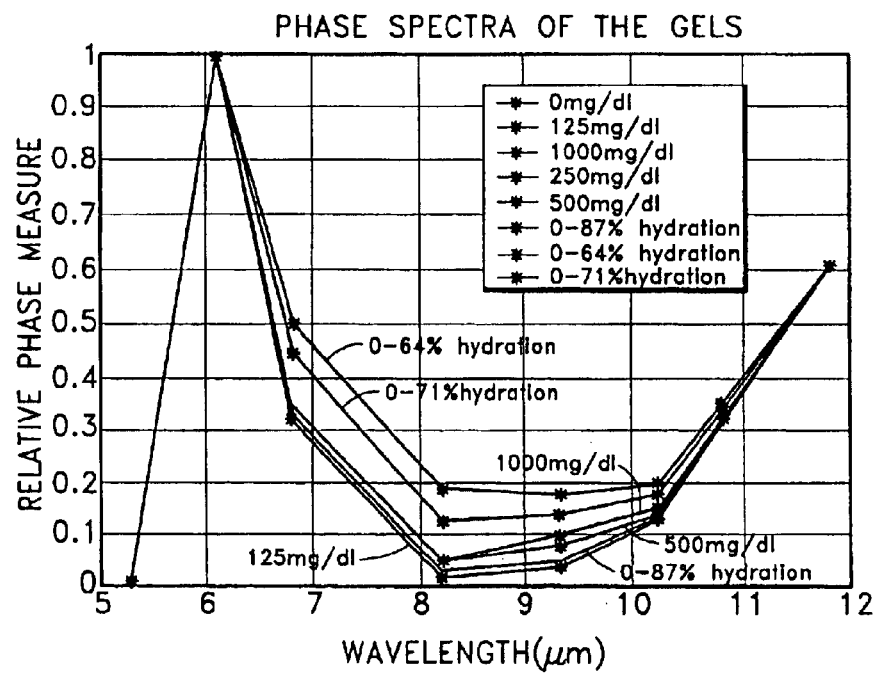
Figure 21:
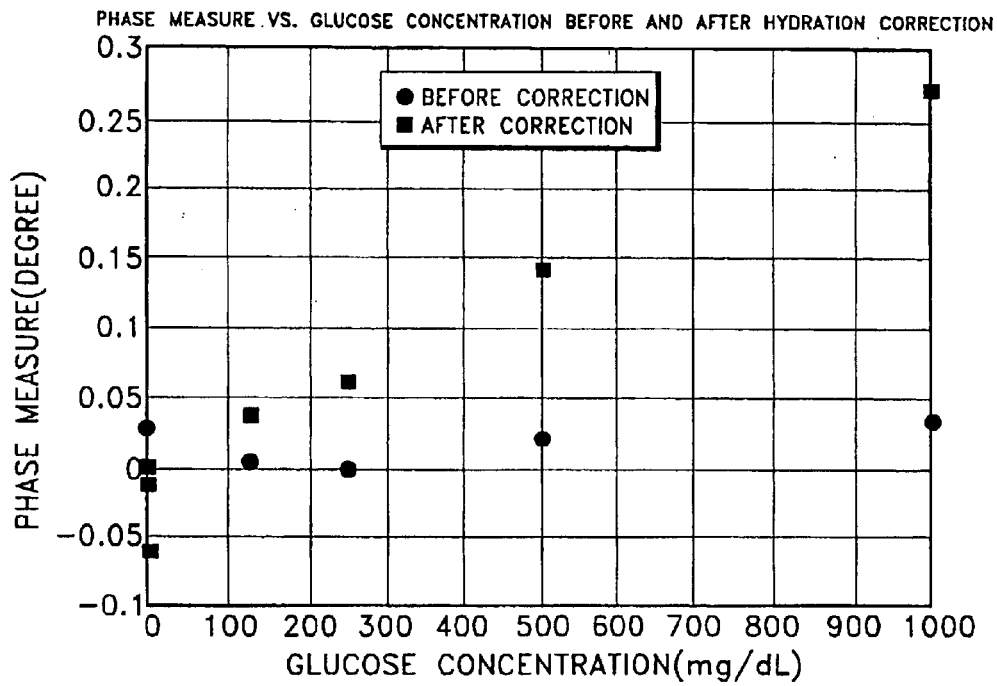
Figure 22:
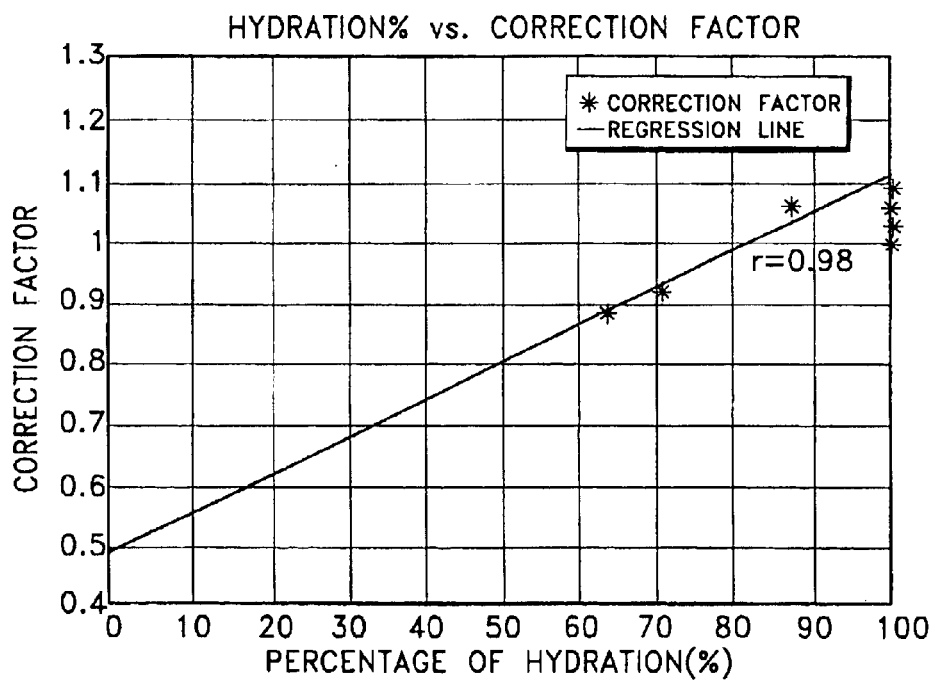
Figure 23:
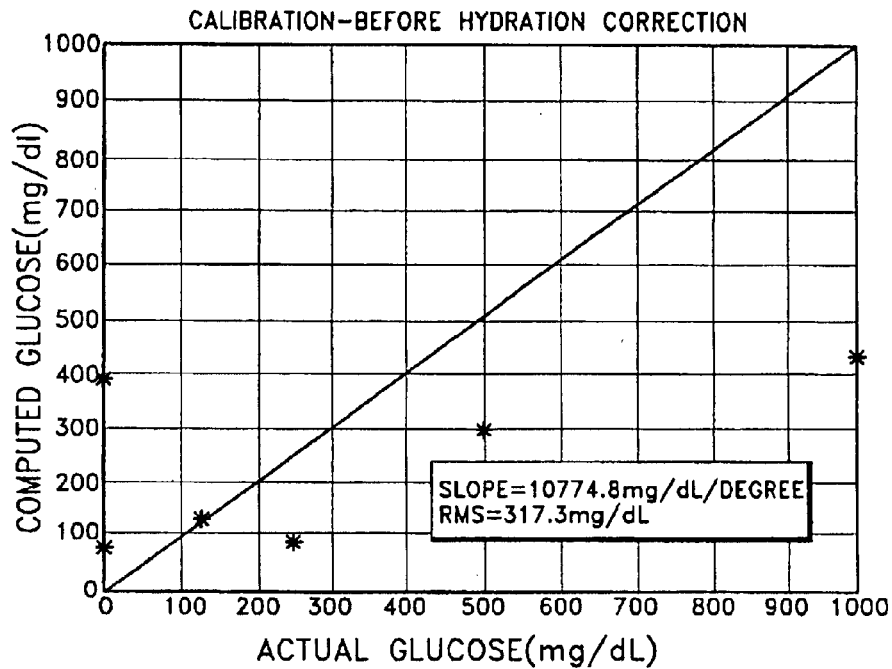
Figure 24:
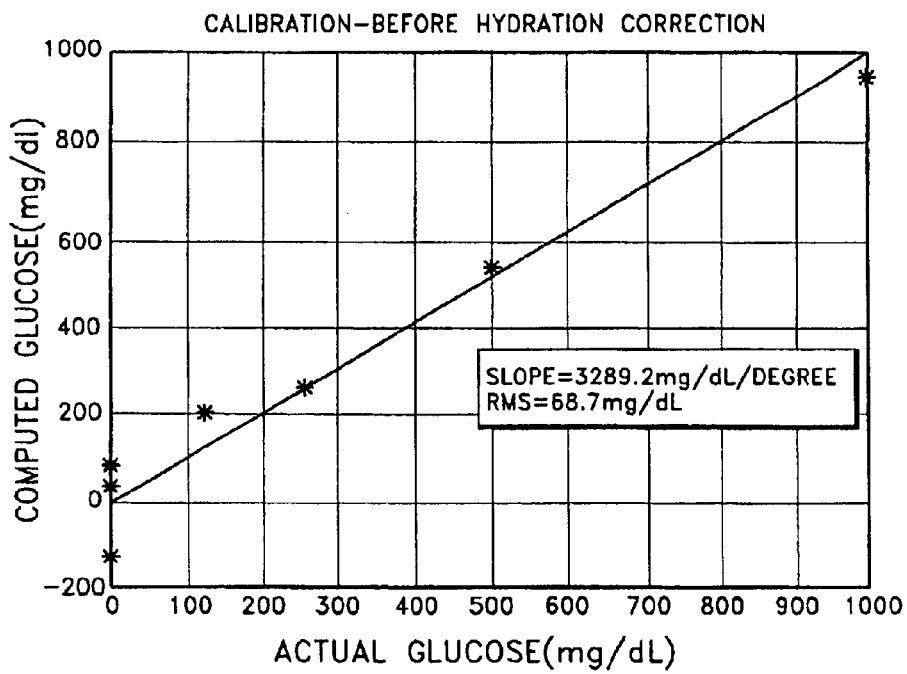

FIG. 20A illustrates a relative phase spectrum of water, plotted as a function of wavelength [μm]. FIG. 20B illustrates the relative spectra of the hydrogels, plotted as a function of wavelength [μm]. As will be apparent to those skilled in the art, the phase spectra of the gels of FIG. 20B are clearly affected by the presence of hydration. FIG. 21 is a graph illustrating phase measure versus glucose concentration before and after hydration correction. FIG. 22 is a graph illustrating the hydration correction coefficient plotted as a function of hydration, and shows a linear regression line with a correlation coefficient of 0.98. It is to be noted that the hydration correction coefficient, or one or more coefficients with which the hydration correction coefficient may be related, may be either linearly or nonlinearly proportional to the measure of hydration. FIGS. 23 and 24 are graphs illustrating computed glucose concentrations [mg/dL] plotted against actual, known glucose concentrations [mg/dL], before and after the hydration correction coefficient is utilized. As shown in FIG. 23, before the hydration correction coefficient is used, the difference between the computed and actual glucose concentrations yields a RMS value of 317.3 mg/dL. After using the hydration correction coefficient, however, the difference between the computed and actual glucose concentrations narrows, yielding a RMS value of 68.7 mg/dL, as shown in FIG. 24.

Although preferred embodiments and methods have been described in detail, certain variations and modifications thereof will be apparent to those skilled in the art, including embodiments and/or methods that do not provide all of the features and benefits described herein. Accordingly, the scope of the above-discussed embodiments and methods is not to be limited by the illustrations or the foregoing descriptions thereof, but rather solely by appended claims.

What is claimed is:

1. A method of analyzing a material sample, said method comprising:
   placing said material sample in operative engagement with an analyte detection system;
   operating said analyte detection system according to an operation algorithm by which said analyte detection system computes a hydration correction coefficient based on changes in electromagnetic energy generated and emitted by at least one of said material sample and a test sample; determines an estimated concentration of an analyte in said material sample; and reduces the effect of a hydration level of said material sample on said estimated concentration.

2. The method of claim 1, further comprising inducing a periodically modulated thermal gradient in said material sample.

3. The method of claim 1, wherein said analyte detection system determines said estimated concentration based on a phase of electromagnetic energy emitted d by said material sample.

4. The method of claim 1, wherein said analyte detection system determines said estimated concentration based on a phase difference between multiple w wavelength-specific signals of electromagnetic energy emitted by said material sample.

5. A method of analyzing a material sample, said method comprising:
   detecting non-reflected electromagnetic energy generated and emitted by at least one of said material sample and a test sample;
   determining a hydration correction coefficient base on aid non-reflected electromagnetic energy;
   placing said material sample in operative engagement with a analyte detection system;
   determining an estimated concentration of an analyte in said material sample; and
   reducing the effect of a hydration level of said material sample on said estimated concentration.

6. The method of claim 5, further comprising inducing a periodically modulated thermal gradient in said material sample.

7. The method of claim 5, wherein determining said estimated concentration comprises measuring a phase of electromagnetic energy emitted by said material sample.

8. The method of claim 5, wherein determining said estimated concentration comprises measuring a phase difference between multiple wavelength-specific signals of electromagnetic energy emitted by said material sample.

9. An analyte detection system comprising:
   a detector array;
   a processing circuit in communication with said detector array; and
   a module executable by said processing circuit whereby said processing circuit computes a hydration correction coefficient based on internal electromagnetic emissions of least one of a material sample and a test sample; computes an estimated concentration of an analyte in said material sample and reduces the effect of a hydration level of said material sample on said estimated concentration.

10. The system of claim 9, wherein said processing circuit computes said estimated concentration based on a phase of electromagnetic energy emitted by said material sample.

11. The system of claim 9, wherein said processing circuit computes said estimated concentration based on a phase difference between multiple wavelength-specific signals of electromagnetic energy emitted by said material sample.

* * * * *

UNITED STATES PATENT AND TRADEMARK OFFICE
CERTIFICATE OF CORRECTION

PATENT NO. : 6,825,044 B2  Page 1 of 1
APPLICATION NO. : 10/301927
DATED : November 30, 2004
INVENTOR(S) : Zheng et al.

It is certified that error appears in the above-identified patent and that said Letters Patent is hereby corrected as shown below:

In Column 1, Line 6, delete "Application" and insert -- Applications --, therefor.

In Column 18, Line 11, delete "1.0 μm." and insert -- 11.0 μm. --, therefor.

In Column 30, Line 60, delete "$\Delta\Phi_{9.5-8.8}{}^G = A_H (\Delta\Phi_{8.4-11.1}{}^G)^2 + B_H (\Delta 101_{8.4-11.1}{}^G)$" and insert -- $\Delta\Phi^G_{9.5-8.4} = A_H(\Delta\Phi^G_{8.4-11.1})^2 + B_H(\Delta\Phi^G_{8.4-11.1})$. --, therefor.

In Column 33, Line 51, Claim 3, after "emitted" delete "d".

In Column 34, Line 3, Claim 4, after "multiple" delete "w".

In Column 34, Line 11, Claim 5, delete "base" and insert -- based --, therefor.

In Column 34, Line 11, Claim 5, delete "aid" and insert -- said --, therefor.

In Colum 34, Line 16, Claim 5, delete "a" and insert -- an --, therefor.

Signed and Sealed this

Twenty-sixth Day of September, 2006

JON W. DUDAS
*Director of the United States Patent and Trademark Office*